(12) United States Patent
Arora et al.

(10) Patent No.: US 8,975,210 B2
(45) Date of Patent: *Mar. 10, 2015

(54) WEB SUBSTRATE HAVING ACTIVATED COLOR REGIONS IN DEFORMED REGIONS

(75) Inventors: Kelyn Anne Arora, Cincinnati, OH (US); John Lee Hammons, Hamilton, OH (US); Timothy Ian Mullane, Union, KY (US)

(73) Assignee: The Procter & Gamble Co., Cincinnati, OH (US)

( * ) Notice: Subject to any disclaimer, the term of this patent is extended or adjusted under 35 U.S.C. 154(b) by 583 days.

This patent is subject to a terminal disclaimer.

(21) Appl. No.: 12/766,698

(22) Filed: Apr. 23, 2010

(65) Prior Publication Data

US 2011/0264064 A1    Oct. 27, 2011

(51) Int. Cl.
| | | |
|---|---|---|
| *B41M 1/26* | (2006.01) | |
| *B41M 5/34* | (2006.01) | |
| *A61F 13/514* | (2006.01) | |
| *G03C 1/76* | (2006.01) | |
| *D06P 7/00* | (2006.01) | |
| *B41M 5/28* | (2006.01) | |
| *D01F 1/04* | (2006.01) | |
| *G03C 1/73* | (2006.01) | |

(52) U.S. Cl.
CPC . *B41M 5/28* (2013.01); *B41M 5/34* (2013.01); *B41M 1/26* (2013.01); *A61F 13/51496* (2013.01); *D01F 1/04* (2013.01); *D06P 7/005* (2013.01); *G03C 1/7642* (2013.01); *G03C 1/73* (2013.01)
USPC .......................... 503/200; 503/206; 430/200

(58) Field of Classification Search
CPC ......... B41M 1/26; B41M 5/34; A61F 13/514; A61F 13/51496; G03C 1/76; G03C 1/7642; D06P 7/00; D06P 7/005
USPC ..................................... 503/204, 206; 430/22
See application file for complete search history.

(56) References Cited

U.S. PATENT DOCUMENTS

| | | | |
|---|---|---|---|
| 3,414,459 | A | 12/1968 | Wells |
| 3,547,723 | A | 12/1970 | Gresham |
| 3,556,907 | A | 1/1971 | Nystrand |
| 3,708,366 | A | 1/1973 | Donnelly |

(Continued)

FOREIGN PATENT DOCUMENTS

| | | |
|---|---|---|
| EP | 0934737 A1 | 8/1999 |
| EP | 1591131 A1 | 11/2005 |

(Continued)

OTHER PUBLICATIONS

International Search Report dated Apr. 14, 2011, 5 pages.

(Continued)

*Primary Examiner* — Bruce H Hess
(74) *Attorney, Agent, or Firm* — Jay Anthony Krebs; Jeffrey V. Bamber; Kim William Zerby

(57) ABSTRACT

The present invention relates to a web substrate comprising an activatable colorant and at least one deformed region. A first activated color region is produced in the web substrate upon exposure to a first external stimulus and a second activated color region is produced within the first activated color region upon exposure to a second external stimulus. The second activated color region coincides with the deformed region.

23 Claims, 19 Drawing Sheets

(56) References Cited

U.S. PATENT DOCUMENTS

| | | |
|---|---|---|
| 3,738,905 A | 6/1973 | Thomas |
| 3,867,225 A | 2/1975 | Nystrand |
| 4,438,167 A | 3/1984 | Schwarz |
| 4,483,728 A | 11/1984 | Bauernfeind |
| 4,705,742 A | 11/1987 | Lewis |
| 4,826,550 A | 5/1989 | Shimizu et al. |
| 4,834,741 A | 5/1989 | Sabee |
| 4,968,313 A | 11/1990 | Sabee |
| 5,143,679 A | 9/1992 | Weber |
| 5,156,793 A | 10/1992 | Buell et al. |
| 5,167,897 A | 12/1992 | Weber et al. |
| 5,197,958 A | 3/1993 | Howell |
| 5,202,173 A | 4/1993 | Wu et al. |
| 5,246,433 A | 9/1993 | Hasse |
| 5,254,111 A | 10/1993 | Cancio et al. |
| 5,296,184 A | 3/1994 | Wu et al. |
| 5,338,504 A | 8/1994 | Wang et al. |
| 5,354,597 A | 10/1994 | Capik et al. |
| 5,464,401 A | 11/1995 | Hasse |
| 5,468,323 A | 11/1995 | McNeil |
| 5,503,076 A | 4/1996 | Yeo |
| 5,518,801 A | 5/1996 | Chappell et al. |
| 5,527,304 A | 6/1996 | Buell |
| 5,575,783 A | 11/1996 | Clear |
| 5,591,155 A | 1/1997 | Nishikawa |
| 5,628,097 A | 5/1997 | Benson et al. |
| 5,628,741 A | 5/1997 | Buell |
| 5,650,214 A | 7/1997 | Anderson et al. |
| 5,658,639 A | 8/1997 | Curro et al. |
| 5,674,216 A | 10/1997 | Buell |
| 5,691,035 A | 11/1997 | Chappell |
| 5,710,094 A | 1/1998 | Minami et al. |
| 5,723,087 A | 3/1998 | Chappell |
| 5,730,961 A | 3/1998 | Goudjil |
| 5,779,691 A | 7/1998 | Schmitt |
| 5,891,544 A | 4/1999 | Chappell |
| 5,916,661 A | 6/1999 | Benson et al. |
| 5,916,663 A | 6/1999 | Chappell |
| 5,968,025 A | 10/1999 | Roe et al. |
| 6,027,483 A | 2/2000 | Chappell |
| 6,080,415 A | 6/2000 | Simon |
| 6,086,715 A | 7/2000 | McNeil |
| 6,092,002 A | 7/2000 | Kastman et al. |
| 6,258,308 B1 | 7/2001 | Brady et al. |
| 6,277,466 B1 | 8/2001 | McNeil et al. |
| 6,306,409 B1 | 10/2001 | Ogawa et al. |
| 6,330,730 B1 | 12/2001 | Davies et al. |
| 6,344,102 B1 | 2/2002 | Wagner |
| 6,368,444 B1 | 4/2002 | Jameson et al. |
| 6,383,431 B1 | 5/2002 | Dobrin et al. |
| 6,395,133 B1 | 5/2002 | McNeil |
| 6,476,289 B1 | 11/2002 | Buell |
| 6,596,669 B1 | 7/2003 | Maruyama et al. |
| 6,710,221 B1 | 3/2004 | Pierce et al. |
| 6,719,742 B1 | 4/2004 | McCormack et al. |
| 6,746,766 B2 | 6/2004 | Bond et al. |
| 6,780,270 B2 | 8/2004 | Andersson |
| 6,794,023 B1 | 9/2004 | Melik et al. |
| 6,811,643 B2 | 11/2004 | McAmish |
| 6,818,295 B2 | 11/2004 | Bond et al. |
| 6,821,612 B1 | 11/2004 | Melik et al. |
| 6,843,949 B2 | 1/2005 | Brady et al. |
| 6,846,172 B2 | 1/2005 | Vaughn et al. |
| 6,849,319 B2 | 2/2005 | Cree et al. |
| 6,911,022 B2 | 6/2005 | Steger et al. |
| 6,946,506 B2 | 9/2005 | Bond et al. |
| 6,984,770 B2 | 1/2006 | Graeme, III et al. |
| 7,183,231 B2 | 2/2007 | Hoying et al. |
| 7,270,861 B2 | 9/2007 | Broering et al. |
| 7,306,582 B2 | 12/2007 | Adams et al. |
| 7,311,696 B2 | 12/2007 | Christon et al. |
| 7,402,157 B2 | 7/2008 | Christon et al. |
| 7,485,403 B2 | 2/2009 | Khan |
| 7,524,404 B2 | 4/2009 | Boatman et al. |
| 2002/0062115 A1 | 5/2002 | Wada et al. |
| 2003/0091803 A1 | 5/2003 | Bond et al. |
| 2003/0109605 A1 | 6/2003 | Bond et al. |
| 2003/0109839 A1 | 6/2003 | Costea et al. |
| 2004/0131820 A1 | 7/2004 | Turner et al. |
| 2004/0170813 A1 | 9/2004 | Digiacomantonia et al. |
| 2004/0265534 A1 | 12/2004 | Curro et al. |
| 2005/0021753 A1 | 1/2005 | Coleman |
| 2005/0064136 A1 | 3/2005 | Turner et al. |
| 2005/0123726 A1 | 6/2005 | Broering et al. |
| 2005/0170726 A1 | 8/2005 | Brunson et al. |
| 2005/0256479 A1 | 11/2005 | Carlucci et al. |
| 2006/0021536 A1 | 2/2006 | Song et al. |
| 2006/0025735 A1 | 2/2006 | Berg, Jr. et al. |
| 2006/0025736 A1 | 2/2006 | Berg, Jr. et al. |
| 2006/0025737 A1 | 2/2006 | Song et al. |
| 2006/0068168 A1 | 3/2006 | Olson et al. |
| 2006/0072429 A1 | 4/2006 | Nagai et al. |
| 2006/0087053 A1 | 4/2006 | ODonnell et al. |
| 2006/0089071 A1 | 4/2006 | Leidig et al. |
| 2006/0246802 A1 | 11/2006 | Hughes et al. |
| 2006/0286343 A1 | 12/2006 | Curro |
| 2007/0154687 A1 | 7/2007 | Luthi et al. |
| 2007/0156106 A1 | 7/2007 | Klofta et al. |
| 2008/0027405 A1 | 1/2008 | Laviz et al |
| 2008/0091162 A1 | 4/2008 | Maldonado et al. |
| 2008/0132865 A1 | 6/2008 | Li et al. |
| 2008/0195072 A1 | 8/2008 | Warner |
| 2008/0206529 A1 | 8/2008 | Veminami et al. |
| 2008/0224351 A1 | 9/2008 | Curro et al. |
| 2008/0228157 A1 | 9/2008 | McKiernan et al. |
| 2008/0233379 A1 | 9/2008 | O'Connor |
| 2008/0234644 A1 | 9/2008 | Hansson et al. |
| 2008/0269704 A1 | 10/2008 | Hansson et al. |
| 2008/0277621 A1 | 11/2008 | MacDonald et al. |
| 2008/0279253 A1 | 11/2008 | MacDonald et al. |
| 2008/0287903 A1 | 11/2008 | Vega et al. |
| 2008/0305328 A1 | 12/2008 | Green et al. |
| 2009/0030390 A1 | 1/2009 | Hammons et al. |
| 2009/0058892 A1 | 3/2009 | VanDemark |
| 2009/0143516 A1 | 6/2009 | MacDonald et al. |
| 2009/0191476 A1 | 7/2009 | Rogers et al. |
| 2009/0191480 A1 | 7/2009 | Rogers et al. |

FOREIGN PATENT DOCUMENTS

| | | |
|---|---|---|
| JP | 2001123088 | 5/2001 |
| JP | 2002138322 | 5/2002 |
| JP | 2003/199791 A | 7/2003 |
| JP | 2007/050145 A | 3/2007 |
| WO | WO-2004057110 A1 | 7/2004 |
| WO | WO-2006/018640 | 2/2006 |
| WO | WO-2006/114600 A3 | 11/2006 |
| WO | WO-2007/001270 A1 | 1/2007 |
| WO | WO-2007/032710 A1 | 3/2007 |
| WO | WO-2007046073 A2 | 4/2007 |
| WO | WO-2007/067103 A1 | 6/2007 |
| WO | WO-2009/081385 A2 | 7/2009 |
| WO | WO-2009/093028 A2 | 7/2009 |
| WO | WO-2009/081385 A2 | 8/2009 |
| WO | WO-2009/112956 A2 | 9/2009 |
| WO | WO-2010017353 A1 | 2/2010 |
| WO | WO-2010029328 A2 | 3/2010 |
| WO | WO-2011/025486 A1 | 3/2011 |
| WO | WO-2011056777 A1 | 5/2011 |

OTHER PUBLICATIONS

International Search Report dated Dec. 9, 2010, 7 pages.

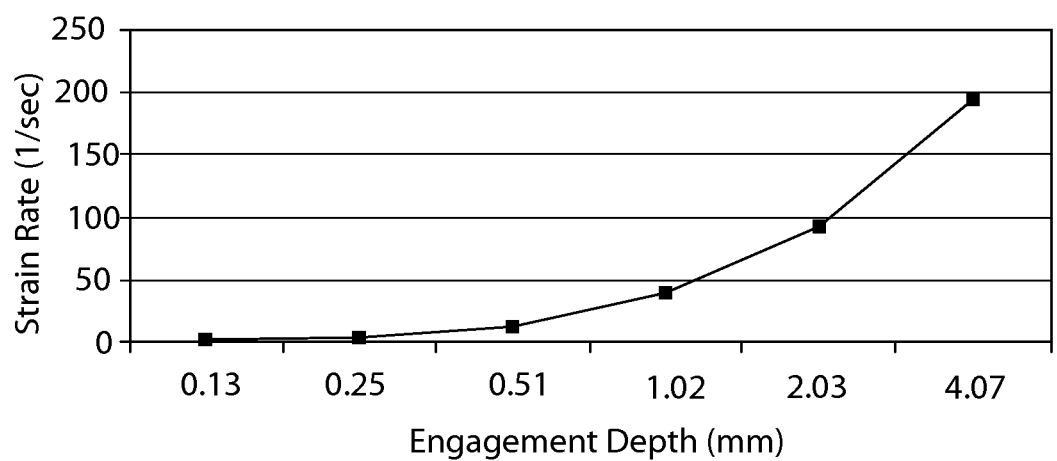
Fig. 17
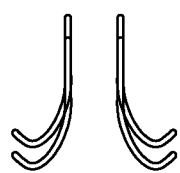  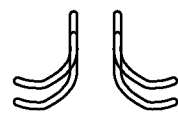
Fig. 18A                Fig. 18B

WEB SUBSTRATE HAVING ACTIVATED COLOR REGIONS IN DEFORMED REGIONS

FIELD OF THE INVENTION

The present invention is related to activatable colorants that are activated to produce color. Specifically, the invention is related to web substrates comprising activatable colorants that are mechanically deformed to produce activated colored regions in mechanically induced deformed regions.

BACKGROUND OF THE INVENTION

A variety of absorbent articles that include different colored regions are available in the market. For instance, absorbent articles such as sanitary napkins and female adult incontinence articles that function to collect fluid discharged from a woman's vagina or urethra sometimes include colored regions to highlight various sections of the absorbent article. For instance the topsheet of the absorbent article may include deformed regions such as apertures proximal the central portion of the absorbent article that are highlighted by color regions that differ in color from portions of the absorbent article remote from the central portion of the absorbent article. Such color regions can be made to provide a perception of depth that corresponds to absorbency. The topsheet may also include other deformed regions such as three dimensional surface structures forming ribs and grooves or tufts in different regions to provide softness and comfort during use. Such three dimensional surfaces can be highlighted by color regions to capture the consumers attentions and enhance the perception of softness. Absorbent articles such as sanitary napkins and diapers have also been known to include decorative designs on other portions of the article such as the backsheet that are appealing to consumers. Such decorative designs can be associated with mechanically deformed regions of the article to highlight functional features such as softness or elasticity.

High speed manufacturing lines can include equipment and processing to produce deformed regions in web substrates during production of articles such as disposable absorbent articles. Such equipment can represent a significant capital cost to manufacturing. Adding printing capability to the manufacturing process in order to highlight the deformed region represents an additional capital cost and complexity in order to register the printing with the deformed regions. For manufacturers to effectively manage the cost, it is advantageous to use existing manufacturing lines to continue manufacturing absorbent articles. In some instances, the approach manufacturers have chosen to provide for colored regions might not be easily adapted to provide for colored regions that coincide with mechanically deformed regions due to the crowded nature of the manufacturing line. Thus, if a manufacturer desires to provide for visual elements on deformed regions of the absorbent article, the manufacturer might have to retool the manufacturing line to provide for additional printing and registration capabilities, thus incurring significant additional capital cost.

With these limitations in mind, there is an unaddressed need for web substrates having mechanically deformed regions that can be manufactured cost effectively using existing manufacturing capability that can be provided with colored regions that coincide with mechanically deformed region. Still further there is a need for providing absorbent articles with colored regions coinciding with deformed regions without requiring additional printing or registration capabilities for registering the colored regions with deformed regions.

SUMMARY OF THE INVENTION

Web substrates comprising activatable colorants and at least one deformed region are disclosed where activated color regions are formed coinciding with the deformed regions. The activatable colorant can have both photoreactive and thermochromic material properties such that it first changes color to a first color upon exposure to electromagnetic radiation such as ultraviolet light and then changes to a second color upon exposure to heat. The heat can be induced by strain associated with mechanical deformation during formation of the deformed regions. The deformed regions formed by mechanical deformation can include out of plane deformed regions comprising ridges and grooves, rib-like elements, tufts and three dimensional cone shaped apertures. The deformed regions can also include two dimensional apertures and bond sites. For apertures, the activated color regions circumscribe the apertures.

In one embodiment, the web substrate comprising an activatable colorant comprises a plurality of second regions comprising deformed regions separated by a first region comprising an undeformed region. The first region comprises a first activated color region and the plurality of second regions are separated by the first region and change color producing second activated color regions that coincide with the deformed regions. The first activated color regions are formed in response to a first external stimulus comprising electromagnetic radiation and the second activated color regions are formed in response to a second external stimulus comprising heat induced by strain during formation of the deformed regions.

In another embodiment, the web substrate comprises an activatable colorant and at least one deformed region. The activatable colorant changes a first color in response to a first external stimulus comprising electromagnetic radiation forming a first activated color region. At least a portion of the first activated color region changes a second color in response to a second external stimulus comprising heat forming a second activated color region. The heat is preferably induced by strain during formation of the at least one deformed region in the first activated color region. The second activated color region coincides with the deformed region.

BRIEF DESCRIPTION OF THE DRAWINGS

These and other features, aspects and advantages of the present invention will become better understood with regard to the following description, appended claims, and accompanying drawings where:

FIG. 17 is a graph showing strain rate varying from low to high in the deformation zone during micro-SELF deformation.

FIG. 18A is a tuft formed in a laminate via micro-SELF deformation according to the strain rate depicted by the graph in FIG. 17.

FIG. 18B is a tuft formed during micro-SELF deformation using high strain rate deformation rolls.

FIG. 20 B is a tuft formed during micro-SELF deformation using high strain rate deformation rolls.

DETAILED DESCRIPTION OF THE INVENTION

Definitions

Figure 1:
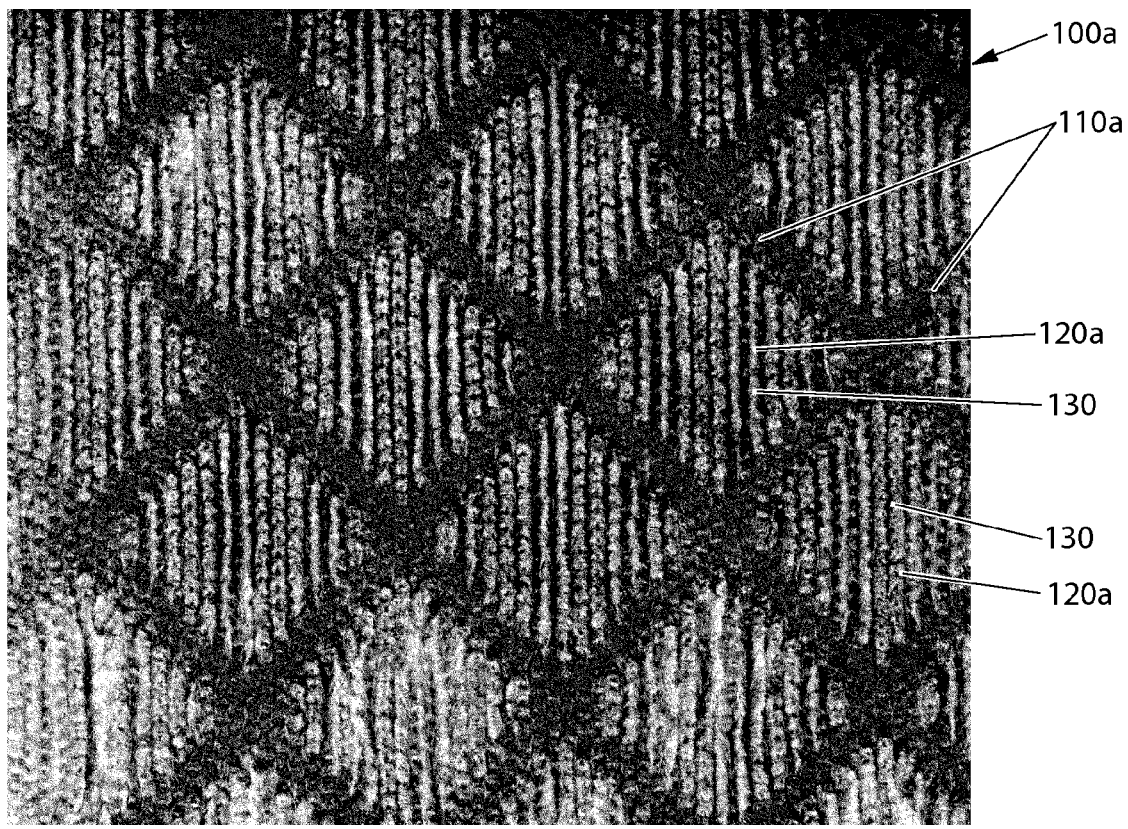
FIG. 1 is a black and white photograph of a web substrate showing second activated color regions separated by first activated color regions.

As used herein and in the claims, the term "comprising" is inclusive or open-ended and does not exclude additional unrecited elements, compositional components, or method steps.

As used herein, "machine direction" means the path that material, such as a web, follows through a manufacturing process.

As used herein "cross direction" means the path that is perpendicular to the machine direction in the plane of the web.

"Absorbent article" means devices that absorb and/or contain liquid. Wearable absorbent articles are absorbent articles placed against or in proximity to the body of the wearer to absorb and contain various exudates discharged from the body. Nonlimiting examples of wearable absorbent articles include diapers, pant-like or pull-on diapers, training pants, sanitary napkins, tampons, panty liners, incontinence devices, and the like. For the purpose of this invention, the term "absorbent article" not only includes the wearable portion of the article but also packaging for individual articles such as release paper wrappers (RPW) and applicators such as tampon applicators. Additional absorbent articles include wipes and cleaning products.

"Mechanical activation" is the mechanical deformation of one or more portions of an extensible material (e.g., film, nonwoven, fiber) that results in permanent elongation of the extensible material in the direction of activation in the X-Y plane of the material. Mechanical activation of a laminate that includes an elastic material joined to an extensible material typically results in one or more portions of the extensible material being at least partially permanently elongated, while the elastic material returns substantially to its original dimension. "Mechanically activated" means a material that has been subjected to an activation process. Suitable examples of absorbent articles, absorbent article components and processes for activation can be found in U.S. Pat. Nos. 5,156,793; 4,438,167; 5,202,173; 5,254,111; 5,296,184; 5,354,597; 6,258,308; 6,368,444; 6,811,643; 6,821,612; 6,843,949; and 6,794,023.

"Direction of mechanical activation" means the direction in which the material is stretched in the X-Y plane during the mechanical activation process. For laminates comprising elastic materials laminated to extensible nonwovens or films, the direction of mechanical activation is also the direction in which the laminate is capable of stretching after completion of the activation process. For materials that do not exhibit elastic behavior, the direction of mechanical activation refers to the direction of the dimension in the X-Y plane of the material that is increased most as a result of the mechanical activation process. Examples of directions of mechanical activation include the machine direction, the cross direction, the longitudinal direction, the lateral direction, and diagonal direction.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaid, and bonded carded web processes, including carded thermal bonding. The basis weight of nonwoven fabrics is usually expressed in grams per square meter (g/m2). The basis weight of a laminate web is the combined basis weight of the constituent layers and any other added components. Fiber diameters are usually expressed in microns; fiber size can also be expressed in denier, which is a unit of weight per length of fiber. The basis weight of laminate webs suitable for use in the present invention can range from 6 g/m2 to 400 g/m2, depending on the ultimate use of the web. For use as a hand towel, for example, both a first web and a second web can be a nonwoven web having a basis weight of between 18 g/m2 and 500 g/m2.

As used herein, "spunbond fibers" refers to relatively small diameter fibers which are formed by extruding molten thermoplastic material as filaments from a plurality of fine, usually circular capillaries of a spinneret with the diameter of the extruded filaments then being rapidly reduced by an externally applied force. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky; to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer composition. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymer compositions extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross sectional area of the fiber and the various polymers are usually not continuous along the entire length of the fiber, instead usually forming fibers which start and end at random. Biconstituent fibers are sometimes also referred to as multiconstituent fibers.

As used herein, the term "non-round fibers" describes fibers having a non-round cross-section, and include "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

"Laminate" means two or more materials that are bonded to one another by methods known in the art, e.g. adhesive bonding, thermal bonding, ultrasonic bonding, extrusion lamination.

As used herein, the term "tampon" refers to any type of absorbent structure such as, e.g., an absorbent mass, that can be inserted into the vaginal canal or other body cavity, such as, e.g., for the absorption of fluid therefrom, to aid in wound healing, and/or for the delivery of materials, such as moisture or active materials such as medicaments. In general, the term "tampon" is used to refer to a finished tampon after the compression and/or shaping process.

As used herein, the term "pledget" refers to an absorbent material prior to the compression and/or shaping of the material into a tampon. Pledgets are sometimes referred to as tampon blanks or softwinds.

As used herein, the term "applicator" refers to a device or implement that facilitates the insertion of a feminine hygiene product, such as, e.g., a tampon or pessary, into an external orifice of a mammal. Suitable applicators include, e.g., telescoping, tube and plunger, and compact applicators.

The term "color" as referred to herein includes any primary color, i.e., white, black, red, blue, violet, orange, yellow, green, and indigo as well as any declination thereof or mixture thereof. The term 'non-color' or 'non-colored' refers to the color white which is further defined as those colors having an L* value of at least 90, an a* value equal to 0±2, and a b* value equal to 0±2.

"Color change" herein means that at least a part of layer including an activatable colorant changes its color in response to an external stimulus. The change in color is visible from outside the layer. A change in color "visible from outside the layer" as used herein means that the color change is detectable by the naked human eye.

"Activatable colorant" means a material which provides a color change in response to an external stimulus.

"External stimulus" means the exposure of the absorbent article to energy from outside the article in the form of pressure, temperature, electromagnetic radiation or combinations thereof.

"Activated color region" means areas containing a colorant that has been activated by external stimulus.

"Deformed region" means a region that has been strained sufficiently to produce distorted regions in the plane and/or out of the plane of the material.

"Visible" means those colors and wavelengths of light that are detectable by the human eye, nominally about 400-700 nanometers in wavelength.

"Electromagnetic radiation" means those areas of the spectrum amenable to industrial applications, such as the ultraviolet through the infrared wavelengths.

"Activatable chemistry" means those chemicals, monomers and polymers which are capable of being affected by an external stimulus.

"Disposable" means absorbent articles that are not intended to be launched or otherwise restored or reused as absorbent articles (i.e., they are intended to be discarded after a single use and, preferably to be recycled, composted or otherwise disposed of in an environmentally compatible manner).

The present invention provides web substrates containing activatable colorants that change color when exposed to external stimuli. The activatable colorant can produce a color change that is reversible or irreversible. However, preferably the activatable colorant according to the present invention produces a color change that is irreversible, thereby providing a permanent visual effect. Sources of activatable colorants include 'thermochromic', which means that the color change is induced by a change of temperature, or 'photoreactive', which means that the color change is induced by electromagnetic radiation, or 'piezochromic', which means that the color change is induced by pressure. Each of these sources of activatable colorants is discussed more fully below. The activatable colorant can also include pH sensitive dyes.

Web substrates can include a combination or blend of two or more activatable colorants where the activatable colorants are the same types but require different levels of external stimuli or the activatable colorants are different types requiring different types of external stimuli. For instance, for substrates including a blend of the same types of activatable colorants, the blend may include two different thermochromic colorants, whereas for substrates including a blend of different types of activatable colorants, the blend might include a thermochromic activatable colorant and a pH sensitive dye. Preferably the web substrate according to the present invention includes a single activatable colorant that is both photoreactive and thermochromic.

The web substrate according to the present invention can also include non activatable colorants in addition to the aforementioned activatable colorants. The non activatable colorant can include $TiO_2$ which is used to increase the opacity of the material. Non activatable colorant can also include a pigment. Pigments can be added to the substrate to provide an initial color which will affect the final color of activated color regions. For instance, a yellow pigment can be added to a substrate having an activatable colorant. If the activatable colorant is ordinarily activated to produce blue, the yellow pigment will cause the activation to produce a green color.

Once activated by an external stimulus, the activatable colorants form activated color regions in the substrate. The activated color regions can comprise uniform colored regions covering large sections or entire areas of the web substrate or nonunifom colored regions comprising varying patterns of colored regions. Alternatively, the activated color regions can include multiple color patterns, zone patterns and multiple shades of a single color. The activatable colorants can also be activated to form activated color regions comprising written text, graphics, and intricate artwork.

The web substrate according to the present invention preferably comprises an activatable colorant that changes to a first color when exposed to a first external stimulus producing a first activated color region and changes to a second color when the first activated color region is subsequently exposed to a second external stimulus producing a second activated color region. Depending on the type of activatable colorant, the first and second external stimuli can comprise heat (which includes heat induced by strain), pressure, electromagnetic radiation, and change in pH. As mentioned above the web substrate according to the present invention preferably comprises an activatable colorant that has both photoreactive and thermochromic properties. The activatable colorant is first activated by a first external stimulus comprising electromagnetic radiation such as ultraviolet light to produce a first activated color region. The first activated color region is subsequently activated by a second external stimulus comprising heat to produce a second activated color region within the first activated color region. The heat is preferably induced by strain.

In a preferred embodiment, the second activated color regions are limited to areas within the first activated color regions. In other words, areas outside the first activated color region that are exposed to the second external stimulus do not change color. For instance, in one embodiment, the substrate can be exposed to a first external stimulus comprising ultraviolet light in a particular pattern such that the first activated color region is limited to certain portions of the substrate. Only those portions forming the first activated color region that are exposed to the second external stimulus comprising heat will change color forming second activated color regions. Portions of the substrate exposed to heat that are outside of the first activated color regions do not change color and therefore, do not form the second activated color region.

As mentioned above, the second external stimulus is preferably heat induced by strain. The strain is preferably caused by mechanical deformation during formation of a deformed region within the first activated color region. Preferably, the second activated color region coincides with the deformed region. The deformed regions formed by mechanical deformation can include out of plane deformed regions comprising ridges and grooves, rib-like elements, tufts, and three dimensional cone shaped apertures. The deformed regions can also include in plane deformed regions comprising mechanically activated regions where the second activated color regions coincide with the mechanically activated regions; bonded regions where the second activated color regions coincide with the bonded regions; or apertures where the second activated color regions circumscribe the apertures. Embodiments illustrating different embodiments of deformed regions and methods of producing deformed regions are discussed more fully below.

The web substrates according to the present invention can comprise films, nonwovens, air laids, fibers, filaments, particles and foams. The activatable colorant can be blended into or coated onto material forming the web substrate and can be disposed throughout or limited to only a portion of the web substrate where a color pattern is desired. The composition used to form the web substrates of the present invention, particularly films and nonwovens can include thermoplastic polymeric and non-thermoplastic polymeric materials. For fibers and nonwovens, thermoplastic polymeric material used in forming fibers must have rheological characteristics suitable for melt spinning. The molecular weight of the polymer must be sufficient to enable entanglement between polymer molecules and yet low enough to be melt spinnable. For melt spinning, thermoplastic polymers have molecular weights below about 1,000,000 g/mol, preferably from about 5,000 g/mol to about 750,000 g/mol, more preferably from about 10,000 g/mol to about 500,000 g/mol and even more preferably from about 50,000 g/mol to about 400,000 g/mol. Unless specified elsewhere, the molecular weight indicated is the number average molecular weight.

The thermoplastic polymeric materials are able to solidify relatively rapidly, preferably under extensional flow, and form a thermally stable fiber structure, as typically encountered in known processes such as a spin draw process for staple fibers or a spunbond continuous fiber process. Preferred polymeric materials include, but are not limited to, polypropylene and polypropylene copolymers, polyethylene and polyethylene copolymers, polyester and polyester copolymers, polyamide, polyimide, polylactic acid, polyhydroxyalkanoate, polyvinyl alcohol, ethylene vinyl alcohol, polyacrylates, and copolymers thereof and mixtures thereof. Other suitable polymeric materials include thermoplastic starch compositions as described in detail in U.S. publications 2003/0109605A1 and 2003/0091803. Other suitable polymeric materials include ethylene acrylic acid, polyolefin carboxylic acid copolymers, and combinations thereof. Other suitable polymeric materials comprising starch and polymers are described in U.S. Pat. Nos. 6,746,766, 6,818,295, and 6,946,506. Common thermoplastic polymer fiber grade materials are preferred, most notably polyester based resins, polypropylene based resins, polylactic acid based resin, polyhydroxyalkonoate based resin, and polyethylene based resin and combination thereof. Most preferred are polyester and polypropylene based resins.

Figure 2:
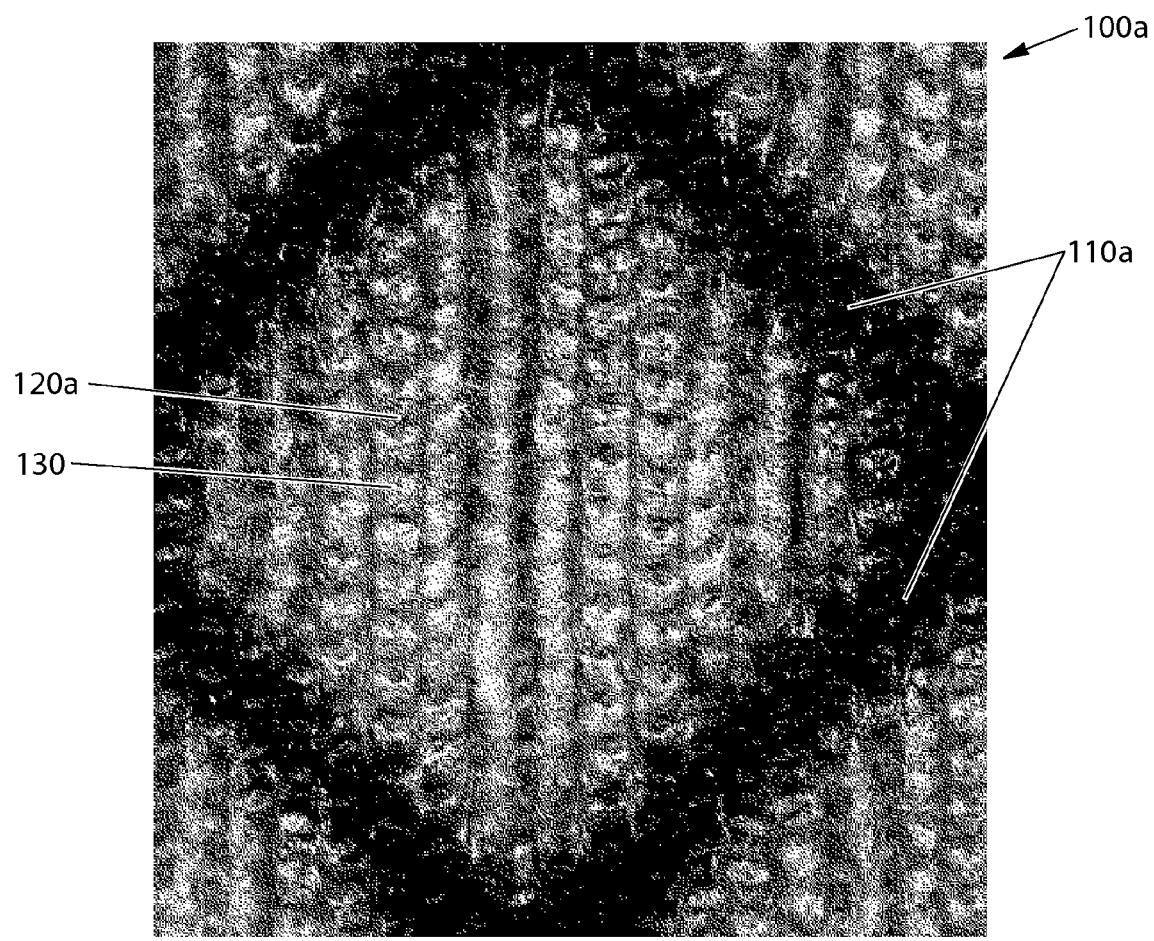
FIG. 2 is a black and white photograph of the web substrate of FIG. 1 showing a magnified view of a second activated color region separated by a first activated color regions.

FIG. 1 and FIG. 2 illustrate an example of a preferred embodiment according to the present invention where the web substrate comprises a nonwoven substrate 100a including a single activatable colorant. The nonwoven substrate 100a was exposed to ultraviolet light to produce a uniform first activated color region 110a throughout the nonwoven substrate 100a. The nonwoven was subsequently mechanically deformed via a SELFing forming a plurality of ridges and grooves 130. The resulting nonwoven substrate 100a has deformed regions comprising a plurality of ridges and grooves 130 forming a plurality of second activated color regions 120a. The second activated color regions 120a are surrounded by first activated color regions 110a comprising undeformed regions.

Figure 3:
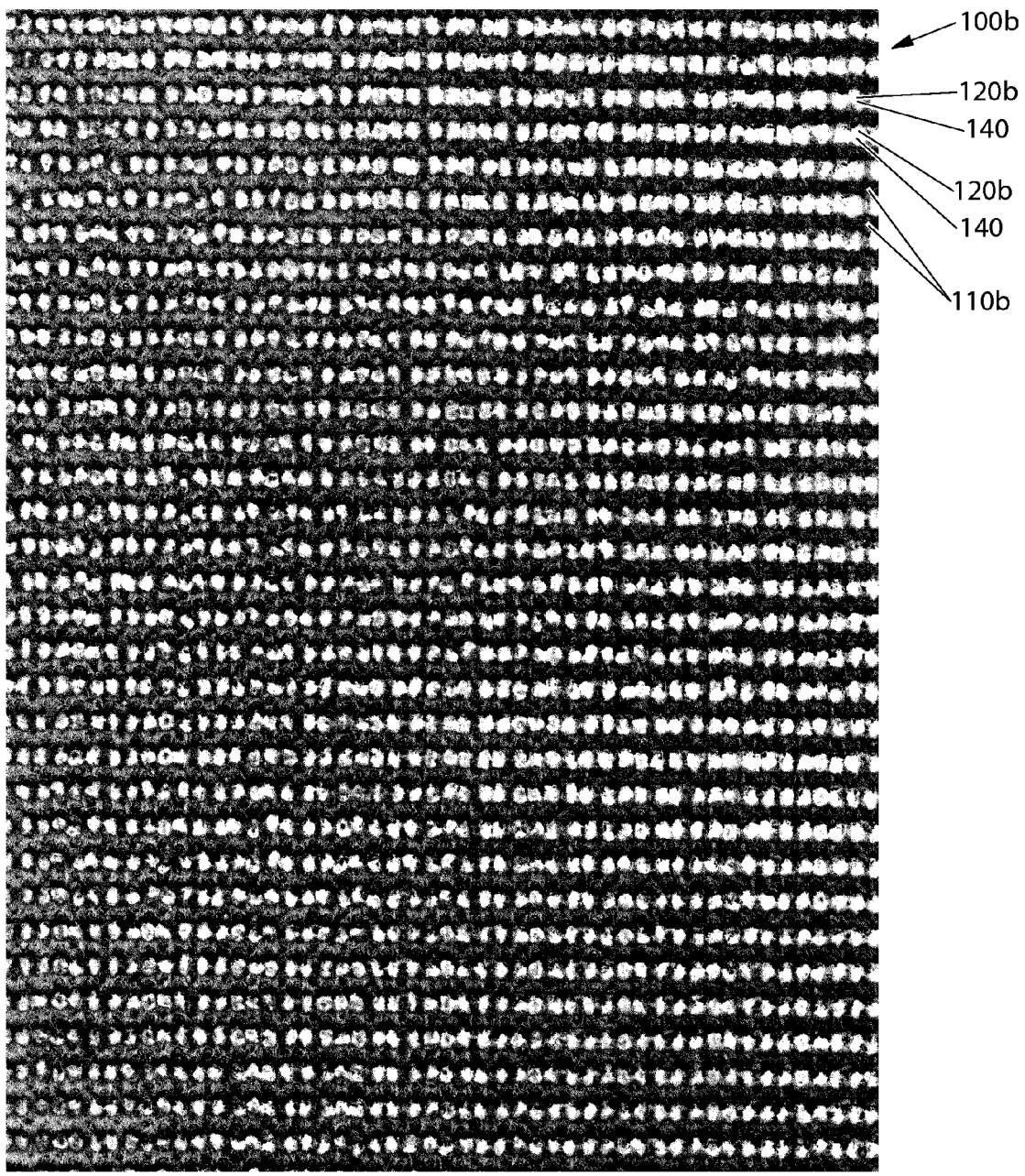
FIG. 3 is a black and white photograph of a web substrate showing second activated color regions comprising tufts separated by first activated color regions.

In an alternate embodiment shown in FIG. 3, the web substrate comprises a nonwoven substrate 100b. The nonwoven substrate 100b was exposed to ultraviolet light to produce a uniform first activated color region 110b throughout the nonwoven substrate 100b. The nonwoven was subsequently mechanically deformed via a micro-SELFing forming a plurality of tufts 140. The resulting nonwoven substrate 100b has deformed regions comprising a plurality of tufts 140 forming a plurality of second activated color regions 120b that coincide with the tufts 140. The plurality of deformed regions comprising second activated color regions 120b are separated by first activated color regions 110b comprising undeformed regions.

Figure 4:
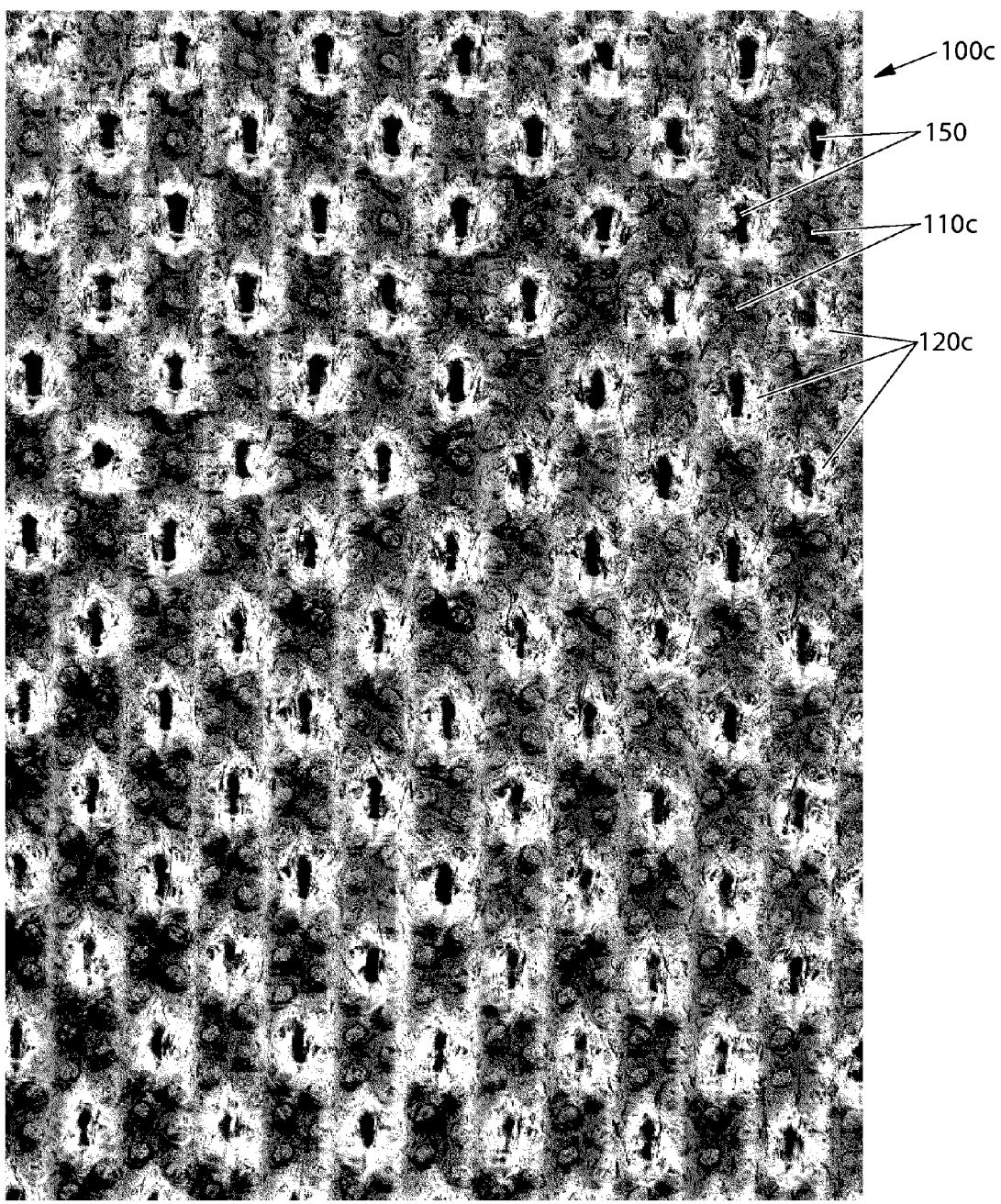
FIG. 4 is a black and white photograph of a web substrate showing second activated color regions comprising perimeters around apertures separated by first activated color regions.

In an alternate embodiment shown in FIG. 4, the web substrate 100c comprising nonwoven was exposed to ultraviolet light to produce a uniform first activated color region 110c throughout the nonwoven substrate 100c. The nonwoven substrate 100c was subsequently mechanically deformed via heated rotary knife aperturing to form a plurality of apertures 150. The resulting nonwoven substrate 100c has deformed regions comprising a plurality of apertures 150 with colored regions around the perimeters of the apertures 150 forming a plurality of second activated color regions 120c. The apertures 150 and corresponding second activated color regions 120c are separated by the first activated color region 110c.

Figure 5:
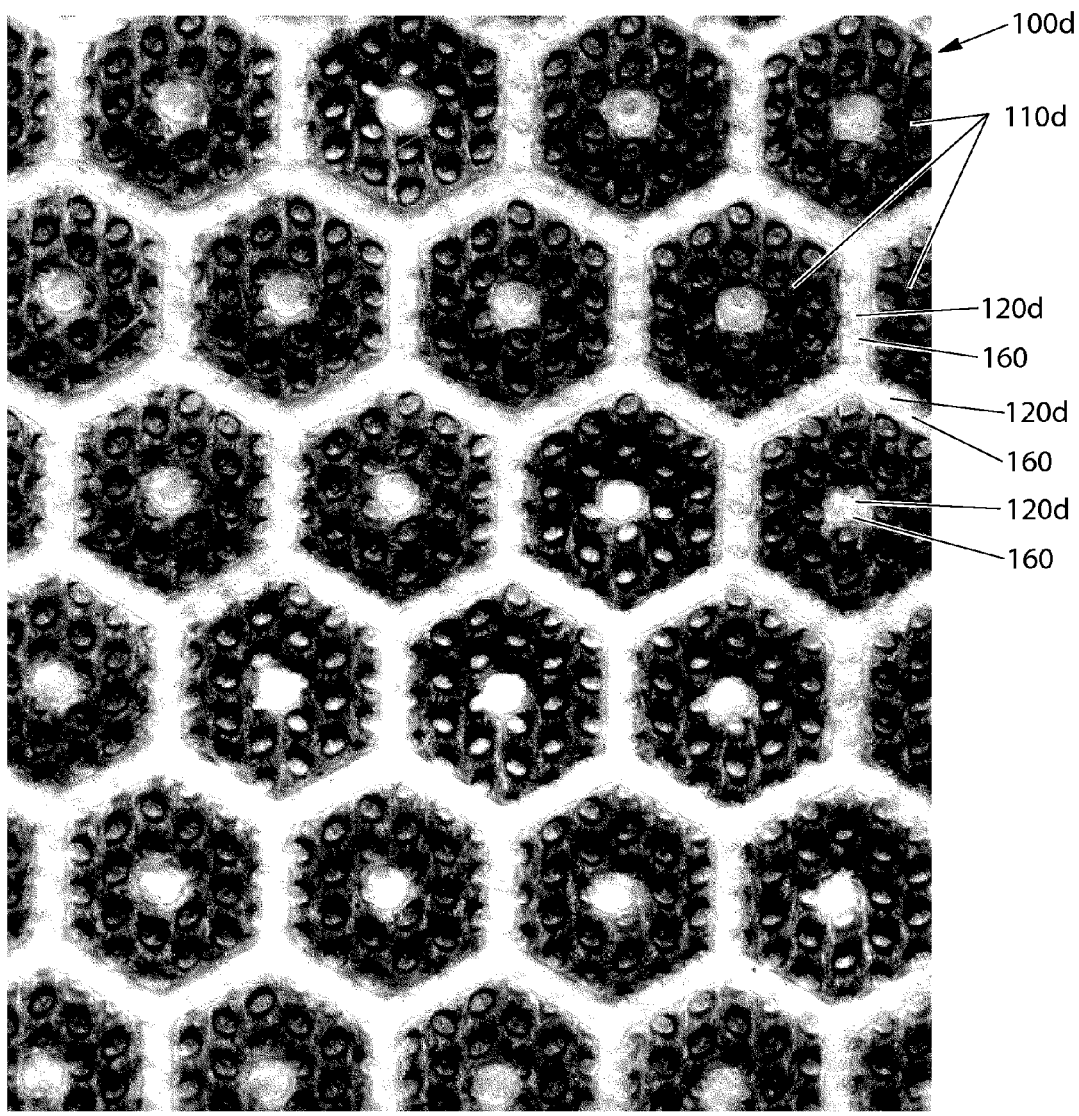
FIG. 5 is a black and white photograph of a web substrate showing first activated color regions separated by second activated color regions comprising bonded regions.

In an alternate embodiment shown in FIG. 5, the web substrate comprising nonwoven substrate 100d was exposed to ultraviolet light to produce a uniform first activated color region 110d throughout the nonwoven substrate 100d and subsequently mechanically deformed via ultrasonic bonding to form a plurality of bond sites 160. The resulting nonwoven substrate has deformed regions comprising a network of bond sites 160 forming a plurality of interconnected second activated color regions 120d. The plurality of second activated color regions 120d separate the first activated color region 110d into a plurality of first activated color regions 110d.

Figure 6:
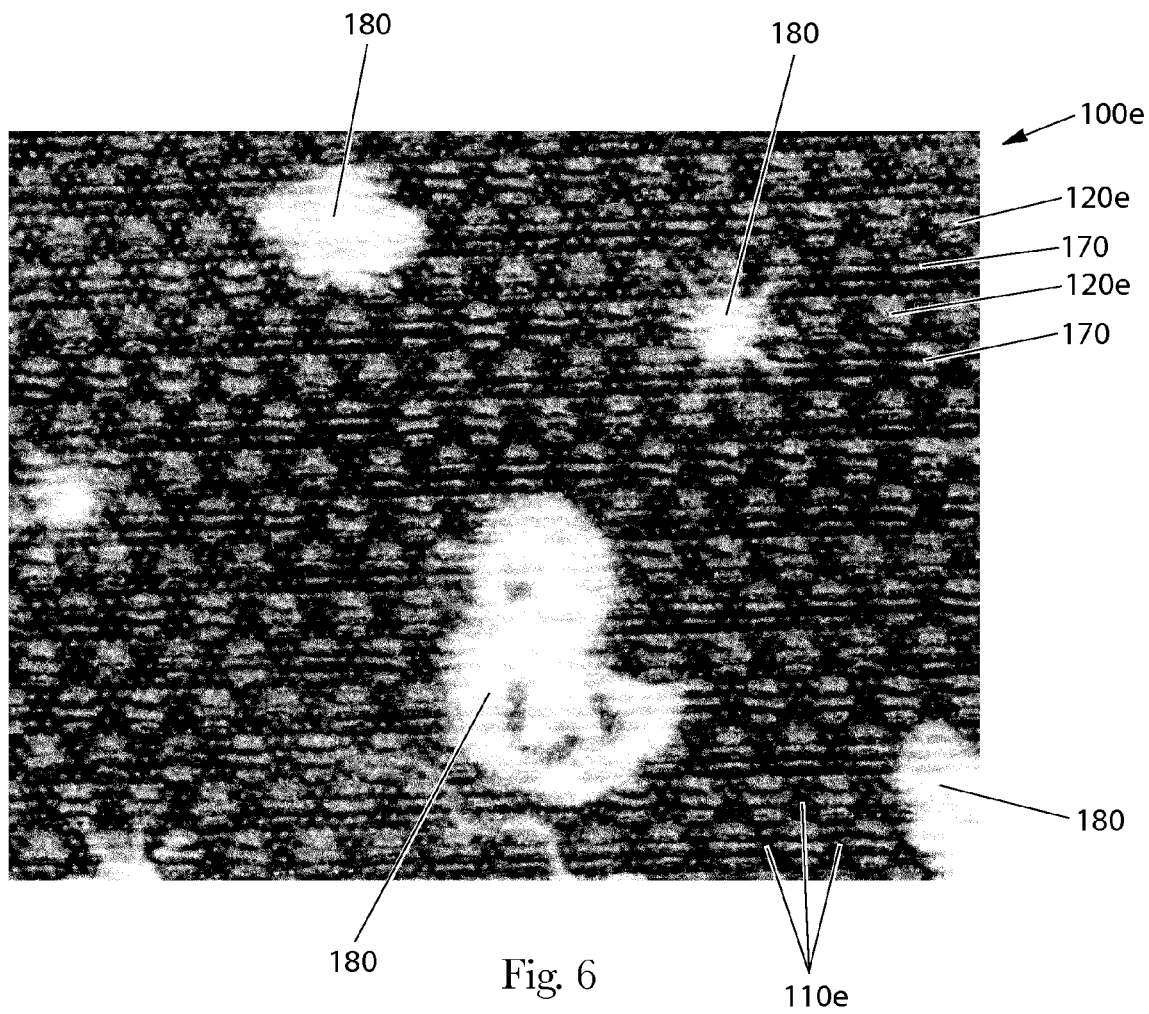
FIG. 6 is a black and white photograph of a web substrate showing second activated color regions separated by first activated color regions including specific images that are separated by and do not form part of either the first activated color region or the second activated color region.

In the embodiment shown in FIG. 6, portions of a nonwoven were masked with specific patterns of images and then exposed to ultraviolet light to produce a first activated color region 110e with specific images 180 disposed within and not forming part of the first activated color region 110e. The nonwoven substrate 100e was subsequently mechanically deformed via SELFing forming deformed regions comprising a plurality of ridges and grooves 170 and a plurality of second activated color regions 120e coinciding with the deformed regions formed within the first activated color regions 110e such that the plurality of second activated color regions 120e are surrounded by first activated color regions 110e comprising undeformed regions and portions of the nonwoven including the specific images 180. The plurality of ridges and grooves 170 forming the deformed regions overlap the portions of the nonwoven including the specific images 180; however, since the portions including the specific images 180 are not included within the first activated color region 110e, they do not change color forming the second activated color regions 120e during formation of the deformed regions.

Activatable Colorant

As briefly described above, activatable colorants can be 'photoreactive', which means that the color change is induced by electromagnetic radiation, 'thermochromic', which means that the color change is induced by a change of temperature, or 'piezochromic', which means that the color change is induced by pressure. These definitions comprise materials changing color irreversibly, reversibly or quasi-reversibly in response to the respective stimulus. The activatable colorants herein can either be coated onto a web substrate, such as on film or nonwoven, or can form an integral part of the substrate by being added e.g. to the polymeric master batch these components are made of. The activatable colorants herein change their color in response to external stimuli as defined hereinbefore.

c) Photoreactive Materials

Photoreactive materials change color in response to exposure to electromagnetic radiation. The color change can be irreversible providing a permanent change in color or it can be reversible providing a temporary change in color.

Photochromic materials are those that reversibly change color when exposed to light or changes in light intensity. Photochromic materials typically provide a reversible color change transiting from a colorless state to a color state upon exposure to light and back to a colorless state when reversed. Examples for photochromic materials are described in U.S. Pat. No. 6,306,409; U.S. Pat. No. 6,080,415 or U.S. Pat. No. 5,730,961.

Polychromic materials are those which are capable of generating multiple colors. Compounds based upon diacetylene, X—C≡C—C≡C—Y, when polymerized, are known to take on different color properties. Polymerization is typically achieved by exposure to certain types of radiation, such as ultraviolet radiation. Varying the intensity of the radiation causes differing degrees of polymerization, and different colors.

It is known that these properties can be utilized to achieve multi-color printing. See, for example; U.S. Pat. No. 4,705,742, "Processless Multicolour Imaging", issued on Nov. 10, 1987, assigned to Gaf Corporation; and WO2006/018640, "Multi-colour printing", published on Feb. 23, 2006, Sherwood Technologies Ltd. Both of these documents disclose methods of applying coatings comprising various diacetylene compounds to the surface of a substrate for the purpose of irradiating and forming an image on the surface of the substrate.

Particularly preferred materials are those that can be dispersed or blended into the polymeric matrix of the layers, such as those disclosed in PCT publication WO 2009/093028A2 and WO 2009/081385 A2, which are compounds which undergo a color change upon irradiation, and which have the general structure: X—C≡C—C≡C—Y—(CO)n-QZ wherein X is H, alkyl or —Y—(CO)n-QW; each Y is the same or a different divalent alkylene group; Q is O, S or NR; R is H or alkyl; W is H, alkyl or Z; each Z is the same or a different unsaturated alkyl group; and each n is 0 or 1.

Another example of a material of use in the present invention is a thermoplastic material comprising polymer mixed with a charge transfer agent and a photo acid generating agent such as those described in US 2009/0191476 A1. Exposure of the thermoplastic material comprising the charge transfer agent and photo acid generating agent to irradiation will bring about a color change reaction which can be used to create text, artwork, devices or other images and effects.

Web substrates according to the present invention preferably comprise photoreactive materials providing an irreversible, permanent change in color. Examples of photoreactive materials providing permanent color change are described in PCT publication WO 2009093028A2 which describes polychromic substances comprising diacetylene compounds that change color when subjected to irradiation. The type of radiation that performs the color change reaction with the diacetylene compounds includes laser or non-coherent, broadband or monochromatic radiation. Specific radiation types include ultraviolet, near, mid or far infrared, visible, microwave, gamma ray, x-ray or electron beam.

Ultraviolet irradiation is preferred for changing substrates comprising the diacetylene compounds from colorless or low visual color to color on exposure to ultraviolet irradiation, and then change to a color different to the first on subsequent exposure to infrared irradiation and/or heat. Heat can be applied directly, for example with heated tooling or the heat may be induced by strain during mechanical deformation of the web substrate. Methods for producing mechanical deformation are discussed more fully below. Methods of laser irradiation may be preferred for writing text and drawing intricate artwork directly on substrates comprising the diacetylene compounds, as laser imaging can be conveniently controlled by computer with the appropriate software and has superior resolution capability. However, similar effects can be obtained by passing radiation from, for example, an ultraviolet lamp through a mask before it reaches the substrates comprising the diacetylene compound.

Another application describing of photoreactive materials providing permanent color change includes WO 2009/081385 which describes thermoplastic material comprising polychromic substance wherein the polychromic substance is a functionalized diacetylene having a formula which has a general structure that is described therein.

Activation of photoreactive materials is preferably achieved using an ultraviolet lamp. One example is the Coil Clean (CC) Series ultraviolet fixtures available from American Ultraviolet (Lebanon, Ind.). Another UVC exposure unit suitable for use in activation of photoreactive materials consists of a metal enclosure containing 8 UV amalgam lamps and 8 ballasts with individual circuits for individual lamp controls and a fan for cooling lamps to maintain temperature. The lamps are 357 mm in length and are available from American Ultraviolet as part number GML750A.

Other examples of equipment that may be used for activation of photoreactive materials include the J3825 MonoCure Lamphead from Nordson UV Limited (Berkshire UK) and the 270S UV Lamp Assembly and Power Supply by Integrated Technology. The type of lamp within the unit may be changed to vary the spectral output as needed. Examples of relevant bulb types include "H", "V", "D" and "Q".

b) Thermochromic Materials

Thermochromic pigments are organic compounds that effectuate a reversible or irreversible color change when a specific temperature threshold is crossed. A thermochromic pigment may comprise three main components: (i) an electron donating coloring organic compound, (ii) an electron accepting compound and (iii) a solvent reaction medium determining the temperature for the coloring reaction to occur. One example of a commercially available, reversible thermochromic pigment is 'ChromaZone® Thermobatch Concentrates available from Thermographic Measurements Co. Ltd. Thermochromic pigments and the mechanism bringing about the temperature triggered color change are well-known in the art and are for example described in U.S. Pat. No. 4,826,550 and U.S. Pat. No. 5,197,958. Other examples of thermochromic pigments are described in published US application 2008/0234644A1.

Thermochromic or temperature sensitive color changing fibers are known from the textile field to be used in clothing, sport equipment, etc. The fibers are either produced by blending a thermochromic pigment in the base resin from which the fibers are to be produced, for example a polyolefin, such as polyethylene or polypropylene, polyester, polyvinyl alcohol etc. or by using a thermochromic coloring liquid for the fibers. The production of temperature sensitive color-changing fibers are disclosed in for example JP2002138322 and JP2001123088. The fibers change color at a selected temperature. The change of color is either reversible or irreversible.

An example of a fiber which can be used according to the invention is a thermochromic fiber which is partly characterized in that the flexural modulus of elasticity of a base resin is within the range of 300-1,500 MPa in the temperature-sensing color-changing fiber. The fiber is formed by melt blending a thermally color-changing pigment in a dispersed state in the base resin of a polyolefin resin and/or the polyolefin resin blended with a thermoplastic resin. The fiber is further described in JP 2002-138322.

Alternatively, the thermosensitive pigment may be of a microcapsule type which is known in the art of thermosensitive pigments.

c) Piezochromic Materials

Any piezochromic materials disclosed in the art are suitable herein as long as they meet the necessary health and safety requirements. An example is disclosed in U.S. Pat. No. 6,330,730.

In one example the piezochromic material is thermochromic and responds to a temperature increase caused by applied pressure. In another example the piezochromic material comprises a dye, which is encapsulated into microcapsules. Upon application of pressure these capsules break and release the dye, which then becomes visible. The color intensity is directly linked to the amount of pressure applied. Typical piezochromic materials require a pressure of from 14 to 140 kPa.

Most typically piezochromic activatable colorants change their color in an irreversible fashion after exertion of pressure. This is due to the fact that the color change was achieved by the destruction of microcapsules, in which the substances for achieving the color change were encapsulated.

Activation of the activatable colorant in the web substrate according to the present can be carried out in a variety of different ways. As previously discussed, the external stimuli activating the activatable colorant in the web substrate according to the present invention includes a first external stimulus comprising electromagnetic radiation that is sequentially followed by a second external stimulus comprising heat. The preferred source of electromagnetic radiation is ultraviolet light and the preferred source of heat is that induced by strain during mechanical deformation. For example, a web substrate can be unwound from a supply roll and exposed to an external stimulus comprising electromagnetic radiation such as ultraviolet light to induce color change and form a first activated color region. Regions within the first activated color region are subsequently exposed to heat producing second activated color regions within the first activated color regions.

The heat producing second activated color regions is preferably induced by strain produced during formation of deformed regions in the first activated color region. The second activated color regions coincide with the deformed regions. The deformed regions can include apertures or bonded regions formed in the x-y plane of the web but preferably include elements protruding in a z direction out of the x-y plane of the web. Bonded regions can be produced via thermal bonding, calendaring, ultrasonic bonding and CPW bonding. Apertures can be formed by a mechanical deformation processes such as rotary knife aperturing. Protruding elements can be formed via mechanical deformation processes including, but not limited to, ring rolling, SELF'ing, micro-SELF, and embossing. Mechanical deformation processes are discussed more fully below.

The heat induced by strain during formation of the deformed regions can result in second activated color regions exhibiting a color gradient which is proportional to the degree of deformation. The color gradient can be produced as a result of variable heat that is produced corresponding to variable strain during formation of the deformed regions. For instance, for a three dimensional deformed regions comprising a tuft formed via micro-SELF, the tuft can comprise a color gradient where the base and tip experience minimal color change since these regions experience little, if any, deformation and corresponding strain during formation of the tufts whereas the sides of the tuft experience heavy strain and corresponding heat resulting in major color change, Mechanical Deformation Processes Mechanical deformation processes use deformation members comprising counter rotating rolls, intermeshing belts or intermeshing two dimensional plates. The deformation members can be at ambient temperature or heated to an elevated temperature above ambient.

Figure 7:
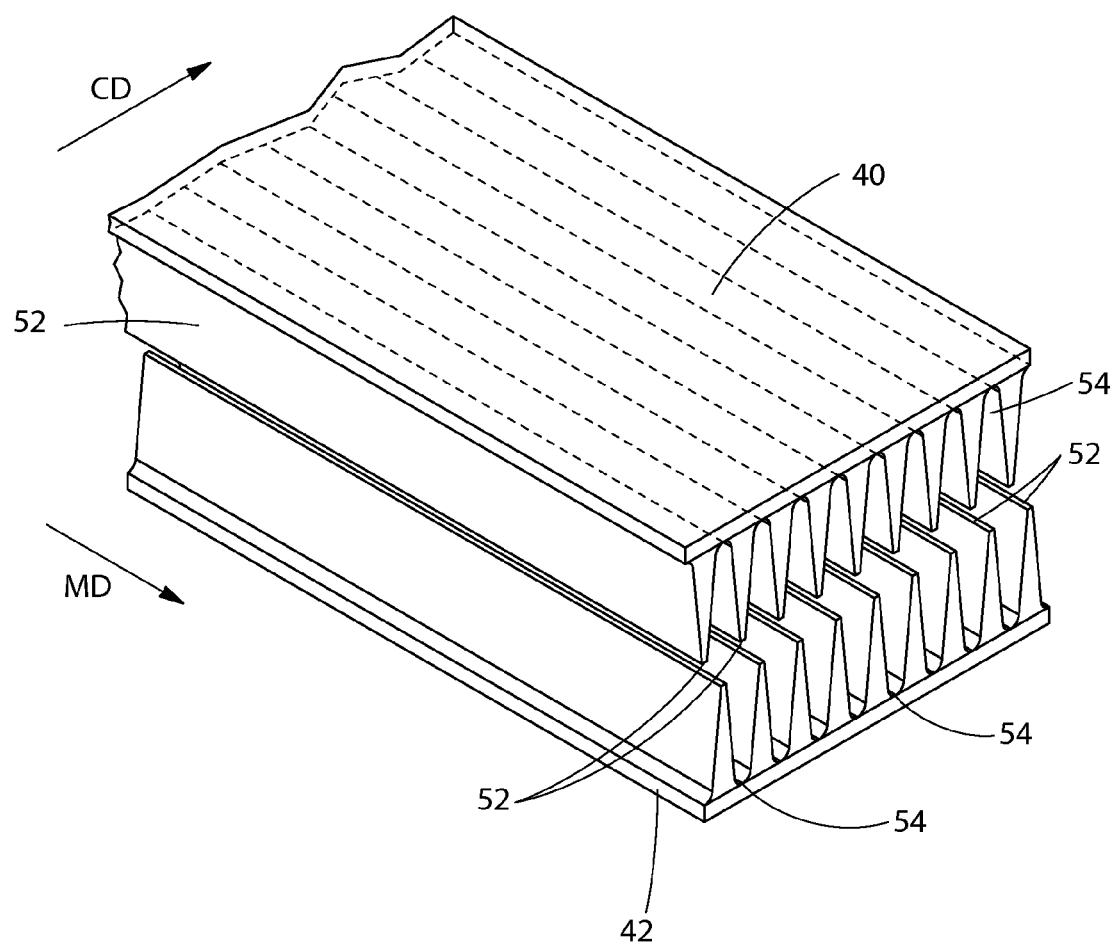
FIG. 7 is a perspective view showing portions of deformation members according to the present invention showing teeth and grooves arranged in a machine direction for incrementally stretching a web in the cross machine direction.
Figure 8:
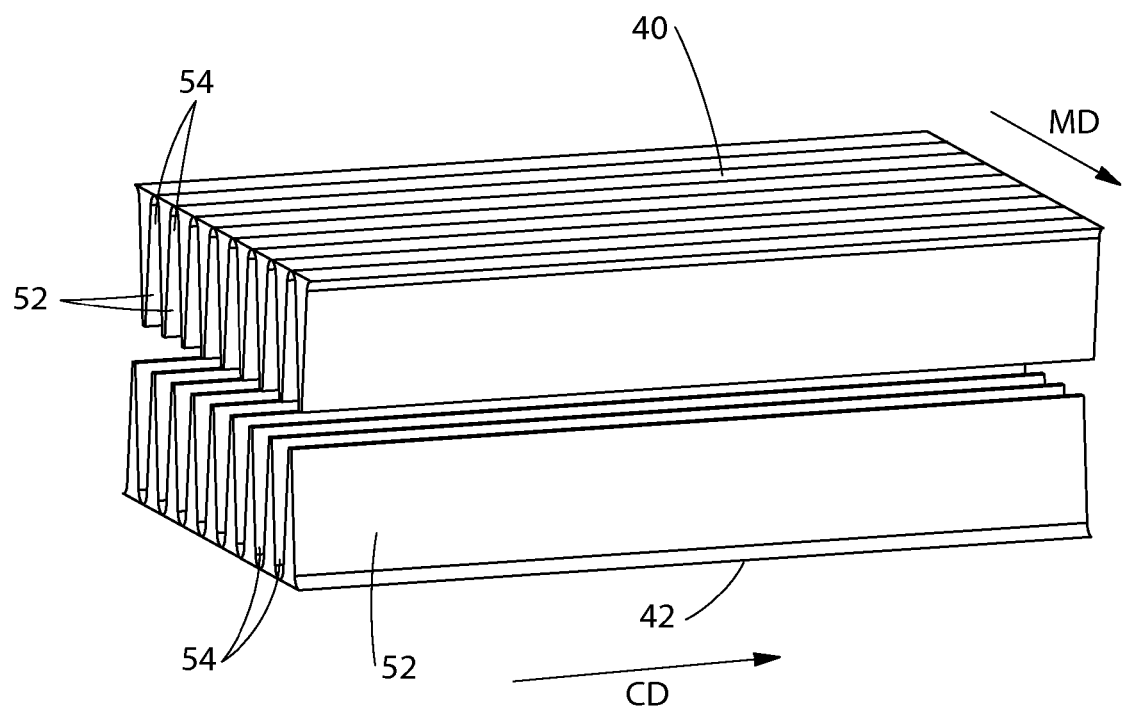
FIG. 8 is a perspective view showing portions of deformation members according to the present invention showing teeth and grooves arranged in a cross machine direction for incrementally stretching a web in the machine direction.

One mechanical deformation process which can be used to produce deformed regions and corresponding heat induced by strain in a web substrate is a process commonly referred to as ring rolling where intermeshing teeth and grooves of deformation members engage and stretch the web interposed therebetween. For ring rolling, the deformation members can be arranged to stretch the web in the cross machine direction or the machine direction depending on the orientation of the teeth and grooves. For instance, for incremental stretching in the cross machine direction CD as shown in FIG. 7, teeth 52 and grooves 54 on each deformation member 40, 42 are oriented in the machine direction MD. Conversely, for incremental stretching in the machine direction MD as shown in FIG. 8, the teeth 52 and grooves 54 on each deformation member 40, 42 are oriented in the cross machine direction CD. Deformation members comprising such cross machine direction teeth and grooves are kept in phase in the machine direction with respect to the intermeshing pattern.

Figure 9:
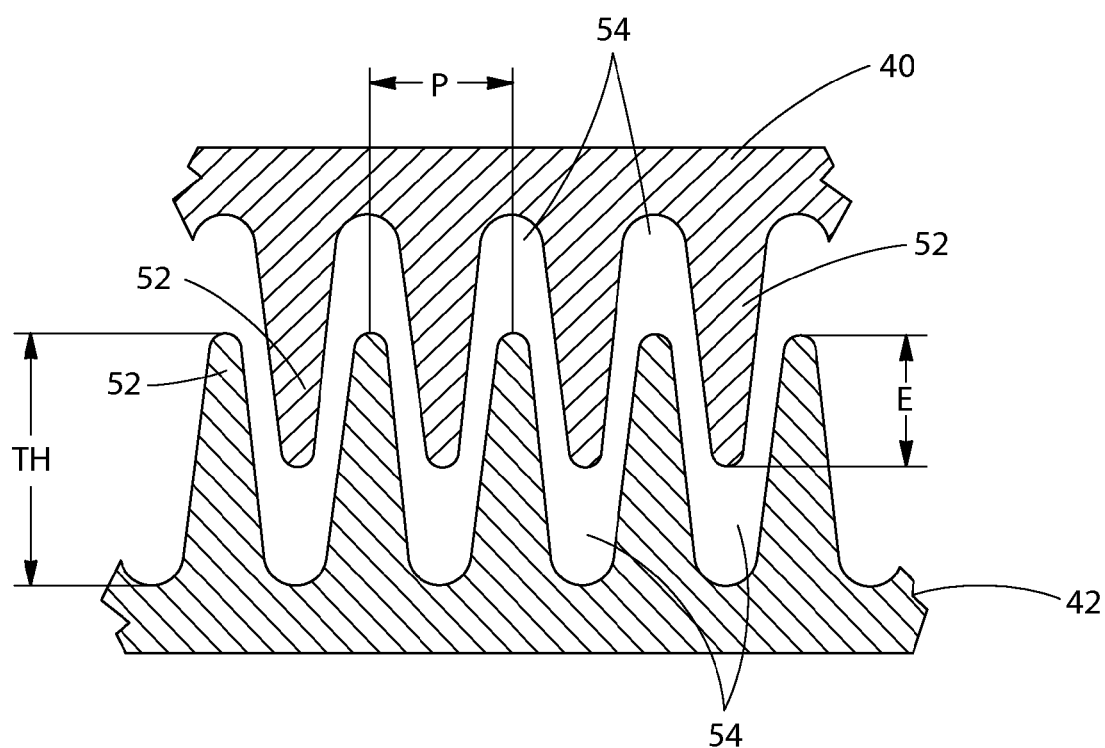
FIG. 9 is an enlarged, fragmentary, cross-sectional view showing the interengagement of teeth and grooves of deformation members as shown in FIG. 7 and FIG. 8.

FIG. 9 is an enlarged, fragmentary, cross-sectional view showing the interengagement of teeth 52 and grooves 54 of respective opposing deformation members 40, 42 in a deformation zone which stretch the web. Teeth 52 have a tooth height TH and are spaced apart from one another by a preferably uniform distance to define a tooth pitch P. As shown, teeth 52 of deformation member 40 extend partially into grooves 54 of the opposed deformation member 42 to define a "depth of engagement", E, as shown in FIG. 9. During deformation, the depth of engagement is controlled to gradually increase over at lease a portion of the deformation zone.

Figure 10:
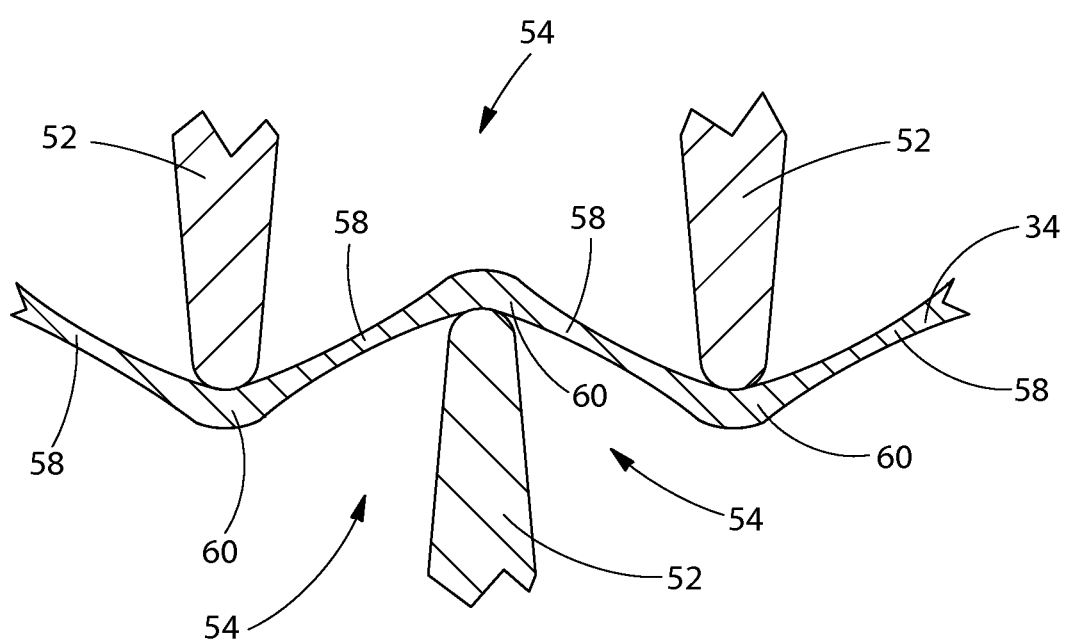
FIG. 10 is an even further enlarged view of the deformation members shown in FIG. 7 and FIG. 8 showing several interengaged teeth and grooves with a web of material therebetween.

FIG. 10 is an even further enlarged view of several interengaged teeth 52 and grooves 54 in the deformation zone with a web 34 of material therebetween. As shown, a portion of a web 34, which can be nonwoven web, is received between the interengaged teeth and grooves in the deformation zone. The interengagement of the teeth and grooves causes laterally spaced portions of web 34 to be pressed by teeth 52 into opposed grooves 54. In the course of passing between deformation members, the forces of teeth 52 pressing web 34 into opposed grooves 54 impose within web 34 tensile stresses that act in the machine or cross machine direction depending on the orientation of the teeth and grooves on the deformation members. The tensile stresses can cause intermediate web sections 58 that lie between and that span the spaces between the tips of adjacent teeth 52 to stretch or extend in a machine or cross machine direction, which can result in a localized reduction of the web thickness at each of intermediate web sections 58. For nonwoven webs, including air laid webs, the stretching can cause fiber reorientation, a reduction in basis weight, and controlled fiber destruction in the intermediate web sections 58.

Although the portions of web 34 that lie between the adjacent teeth are locally stretched, the portions of the web that are in contact with the tips of the teeth may not undergo a similar degree of extension. Because of the frictional forces that exist between the surfaces at the rounded outer ends of teeth 52 and the adjacent areas 60 of web 34 that are in contact with the tooth surfaces at the outer ends of the teeth, sliding movement of those portions of the web surfaces relative to the tooth surfaces at the outer ends of the teeth is minimized. Consequently, in some cases, the properties of the web 34 at those areas of the web that are in contact with the surfaces of the tooth tips change only slightly, as compared with the change in web properties that occur at intermediate web sections 58.

Teeth 52 can be generally triangular in cross section having generally rounded tooth tips, as shown in FIGS. 9 and 10. As shown teeth 52 have a tooth height TH (note that TH can also be applied to groove depth; in one embodiment tooth height and groove depth can be equal), and a tooth-to-tooth spacing referred to as the pitch P. The depth of engagement E, tooth height TH, and pitch P can be varied as desired depending on the properties of the webs being processed and the desired characteristics of the processed webs.

As will be appreciated by those skilled in the art, the sizes of the respective teeth and grooves can be varied within a wide range and would still be effective to carry out the present invention. In that regard, additional structural details of suitable deformation members according to the present invention are provided in U.S. Pat. No. 5,156,793, entitled "Method for Incrementally Stretching Zero Strain Stretch Laminate Sheet in a Non-Uniform Manner to Impart a Varying Degree of Elasticity Thereto," which issued on Oct. 20, 1992, to Kenneth B. Buell et al.; and in U.S. Pat. No. 5,167,897 entitled "Method for Incrementally Stretching a Zero Strain Stretch Laminate Sheet to Impart Elasticity Thereto," which issued on Dec. 1, 1992, to Gerald M. Weber et al. Other Activation patents include: U.S. Pat. No. 5,527,304, entitled "Absorbent Article with Elasticized Side Panels having Extension Panel," which issued on Jun. 18, 1996, to Buell; U.S. Pat. No. 5,674,216, entitled "Absorbent Article with Elasticized Side Panels," which issued on Oct. 7, 1997, to Buell; U.S. Pat. No. 6,476,289, entitled "Garment having Elastomeric Laminate," which issued on Jun. 18, 1996, to Buell; U.S. Pat. No. 5,628,741, entitled "Absorbent Article with Elastic Feature having a Prestrained Web Portion and Method for Forming Same," which issued on May 13, 1997, to Buell; U.S. Pat. No. 5,591,155, entitled "Disposable Training Pant having Improved Stretchable Side Panels," which issued on Jan. 7, 1997, to Nishikawa; U.S. Pat. No. 5,246,433, entitled "Elasticized Disposable Training Pant and Method of making the Same," which issued on Sep. 21, 1993, to Hasse; U.S. Pat. No. 5,464,401, entitled "Elasticized Disposable Training Pant having Differential Extensibility," which issued on Sep. 21, 1993, to Hasse; U.S. Pat. No. 5,575,783, entitled "Absorbent Article with Dynamic Elastic Feature Comprising Elasticized Hip Panels," which issued on Nov. 19, 1996, to Clear; U.S. Pat. No. 5,779,691, entitled "Fastening Tape for a Sanitary Article Particularly Disposable Diaper," which issued on Jul. 14, 1998, to Schmitt; U.S. Pat. No. 5,143,679, entitled "Method for Sequentially Stretching Zero Strain Stretch Laminate Web to Impart Elasticity thereto Without Rupturing the Web," which issued on Sep. 1, 1992, to Weber; U.S. Pat. No. 4,834,741, entitled "Diaper with Elastic Waist Band Elastic," which issued on May 30, 1989, to Sabee; and U.S. Pat. No. 4,968,313, entitled "Diaper with Elastic Waist Band Elastic," which issued on Nov. 6, 1989, to Sabee.

Another process for mechanically deforming a web which can produce the deformed regions and corresponding heat induced by strain of the present invention is a process commonly referred to as a "SELF" or "SELF'ing", where SELF stands for Structural Elastic Like Film. While the process was originally developed for deforming polymer film to have beneficial structural characteristics, it has been found that the SELF'ing process can be used to produce beneficial structures in nonwoven webs.

Figure 11:
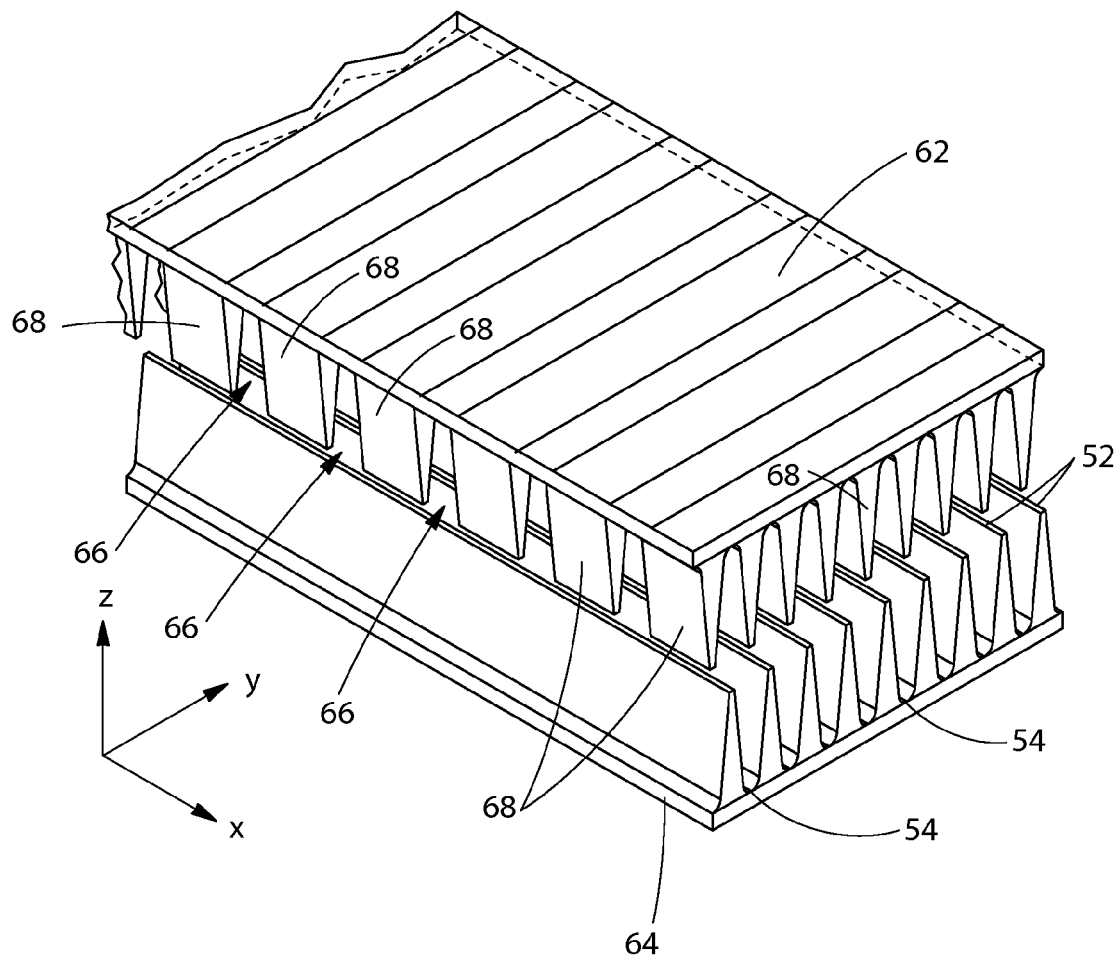
FIG. 11 is a perspective view showing portions of deformation members according to the present invention for use in a SELF process.

Referring to FIG. 11, there is shown a configuration of deformation members for use in a SELF process that can be employed to expand portions of a nonwoven web in the web thickness dimension, by expanding portions of the web out of the X-Y plane in the Z-direction. As shown in FIG. 11, one deformation member 64 includes a plurality of longitudinally-extending, laterally-spaced teeth 52 and grooves 54. Deformation member 62 includes a plurality of longitudinally extending, laterally-spaced teeth 68 wherein portions of the teeth 68 of deformation member 62 have been removed to form notches 66 that define a plurality of spaced teeth 68. As shown in FIG. 11, notches 66 on respective transversely adjacent teeth 68 can be aligned laterally to define a plurality of spaced groups of notched regions about the surface of the deformation member 62. The respective laterally-extending groups of notched regions each extend parallel to the cross machine direction CD of the deformation member 62. Teeth 68 can have a tooth height corresponding to tooth height TH, and a tooth pitch corresponding to the tooth pitch P as previously described in reference to FIG. 9.

As a web passes through a deformation zone formed by deformation members in a SELF process, the teeth 68 of deformation member 62 presses a portion of the web out of plane to cause permanent, localized Z-direction deformation of the web. But the portion of the web that passes between the notched regions 66 of deformation member 62 and the teeth 68 of deformation member 62 will be substantially unformed in the Z-direction, i.e., the web will not be deformed or stretched in that area to the same degree as that of the toothed regions, and can remain substantially planar, while the portions of the web passing between toothed regions of deformation member 62 and the teeth 52 of deformation member 64 can be deformed or stretched beyond the elastic limit of the nonwoven, resulting in a plurality of deformed, raised, rib-like elements.

Figure 12:
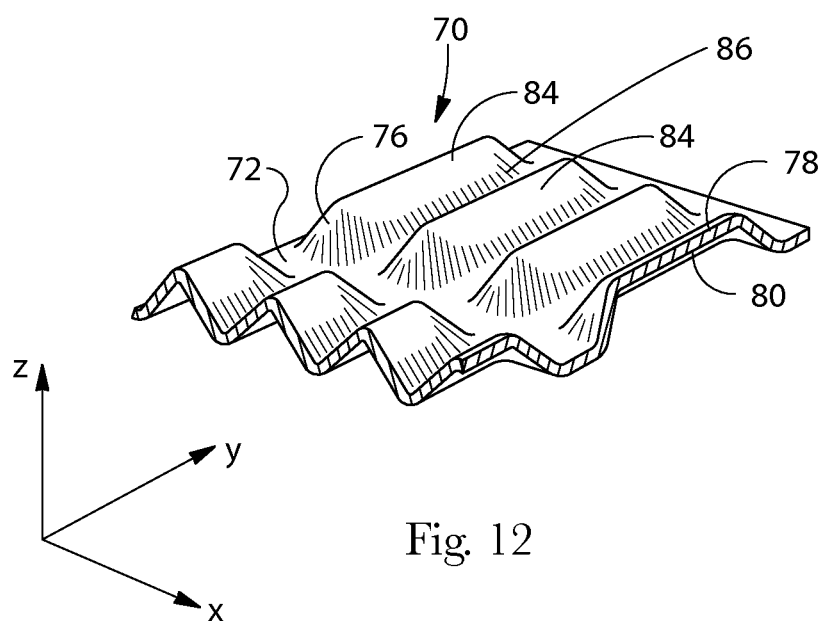
FIG. 12 is a schematic representation of a web after it has passed between a pair of intermeshing SELF rolls.

Referring now to FIG. 12, there is shown a schematic representation of a portion of a SELF'ed web 70 after it has passed between a pair of opposed, interengaged deformation members 62 and 64 of a SELF process, the deformation members having the tooth configurations similar to that shown in FIG. 11. SELF'ed web 70 includes a network of distinct regions. The network includes at least a first region 72, a second region 84, and a transitional region 76, which is at the interface between the first region 72 and the second region 84. SELF'ed web 70 also has a first surface 78 and an oppositely-facing second surface 80. In the embodiment shown in FIG. 12, SELF'ed web 70 includes a plurality of substantially flat spaced first regions 72 and a plurality of alternating rib-like elements forming the second region 84.

In the embodiment shown in FIG. 12, first regions 72 are substantially planar. That is, the material within first regions 72 is substantially flat and is in substantially the same condition after the modification step undergone by a web by passage between deformation members 62 and 64 shown in FIG. 11 as it was in before the web was passed between the deformation members.

Figure 13:
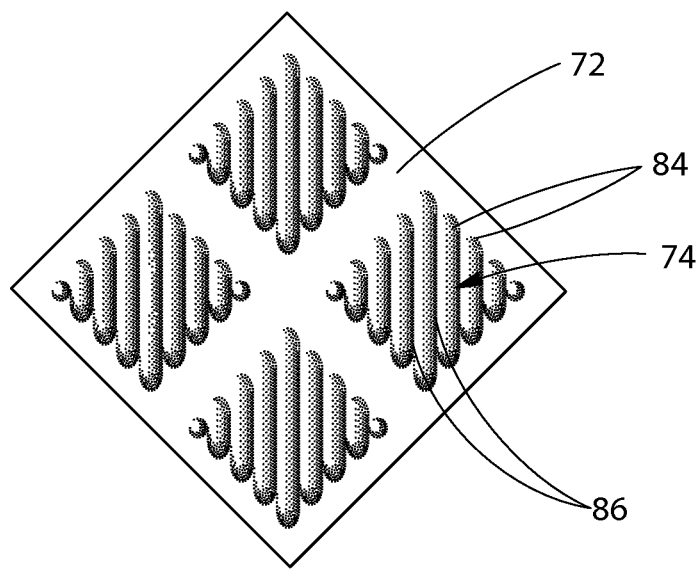
FIG. 13 is a pattern that can be produced in a web by passing the web between a pair of intermeshing SELF deformation members.

In addition to the surface pattern illustrated in FIG. 12 in the form of rib-like elements each having substantially equal lengths and arranged in rows to define generally rectangular areas of deformation separated by linear first regions 72, the desired formation of a web can, if desired, be effected by other deformation member tooth and groove configurations that can cause localized stretching and/or deformation of the web material. For example, as shown in FIG. 13, instead of spaced rectangular arrays of rib-like elements the deformation pattern can be in the form of rib-like elements defining an array of spaced, diamond-shaped second regions 74 with intervening undeformed first regions 72. Each such diamond-shaped second region 74 is defined by alternating rib-like elements 84 and intervening valleys 86. Examples of methods and apparatus for formation of such diamond-shaped elements are disclosed in U.S. Pat. No. 5,650,214, entitled, "Sheet Materials Exhibiting Elastic-Like Behavior and Soft, Cloth-Like Texture," which issued on Jul. 22, 1997, to Barry J. Anderson, et al., and U.S. Pat. No. 6,383,431, entitled, "Method of Modifying a Nonwoven Fibrous Web For Use as a Component of a Disposable Absorbent Article," which issued May 7, 2002, to Dobrin, et al.

Figure 14:
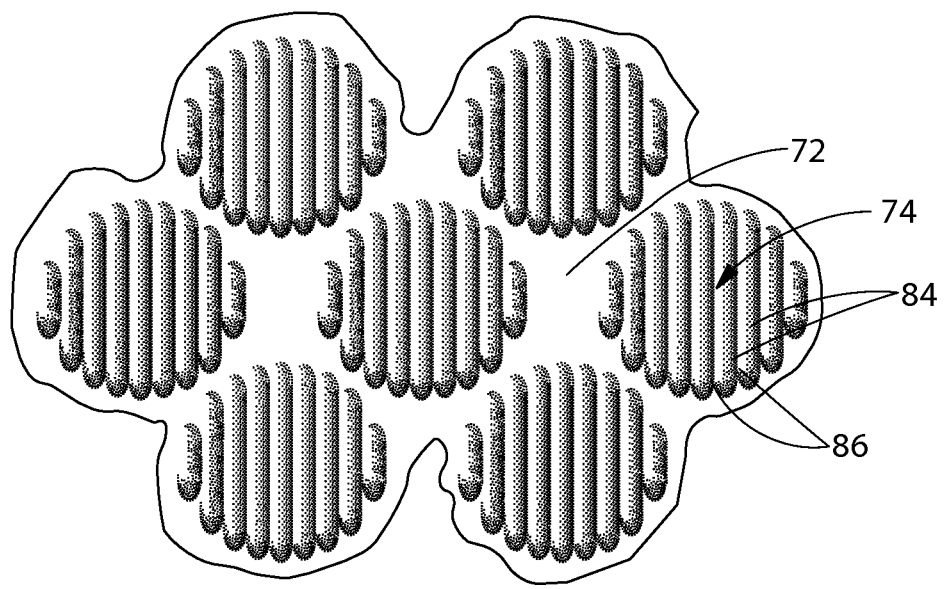
FIG. 14 is a pattern that can be produced in a web by passing the web between a pair of intermeshing SELF deformation members.

As shown in FIG. 14, the deformation pattern can also be in the form of rib-like elements 84 that together define an array of spaced, circularly-shaped second regions 74. Each such circular element can be defined by appropriately spaced, varying-length rib-like elements 84 and intervening valleys 86. Between respective circularly-shaped second regions 74 are unformed intervening first regions 72. As will be apparent to those skilled in the art, other deformation patterns can also be employed, if desired, such as those illustrated and described in U.S. Pat. No. 5,518,801, entitled "Sheet Materials Exhibiting Elastic-Like Behavior," which issued on May 21, 1996, to Charles W. Chappell et al. Other patents issued to Chappell include U.S. Pat. No. 5,691,035 entitled "Web Materials Exhibiting Elastic-like Behavior," issued Nov. 25, 1997; U.S. Pat. No. 5,723,087 entitled "Web Materials Exhibiting Elastic-like Behavior," issued Mar. 3, 1998; U.S. Pat. No. 5,891,544 entitled "Web Materials Exhibiting Elastic-like Behavior" issued Apr. 6, 1999; U.S. Pat. No. 5,916,663 entitled "Web Materials Exhibiting Elastic-like Behavior," issued Jun. 29, 1999; and U.S. Pat. No. 6,027,483 entitled "Web Materials Exhibiting Elastic-like Behavior" issued Feb. 22, 2000.

Another process for mechanically deforming a web which can produce deformed regions and corresponding heat induced by strain of the present invention is a process that can best be described as "micro-SELF". Micro-SELF is a process that is similar in apparatus and method to that of the SELF process described with reference to FIG. 11. The main difference between SELF and micro-SELF is the size and dimensions of the teeth 68 on the toothed deformation member, i.e., the micro-SELF deformation member 82 in FIG. 15, which corresponds to deformation member 62 of FIG. 11. The micro-SELF deformation member 82 can be one of the deformation members forming the deformation zone in a preferred configuration having one patterned deformation member, e.g., micro-SELF deformation member 82, and one non-patterned grooved deformation member (not shown). However, in certain embodiments it may be preferable to use two micro-SELF deformation members 82 having either the same or differing patterns, in the same or different corresponding regions of the respective deformation members. Such an apparatus can produce webs with deformed regions that, in nonwoven webs, can be described as tufts protruding from one or both sides of the processed web. The tufts can be closely spaced, but at least at their base can be spaced apart sufficiently to define void regions between tufts.

Figure 15:
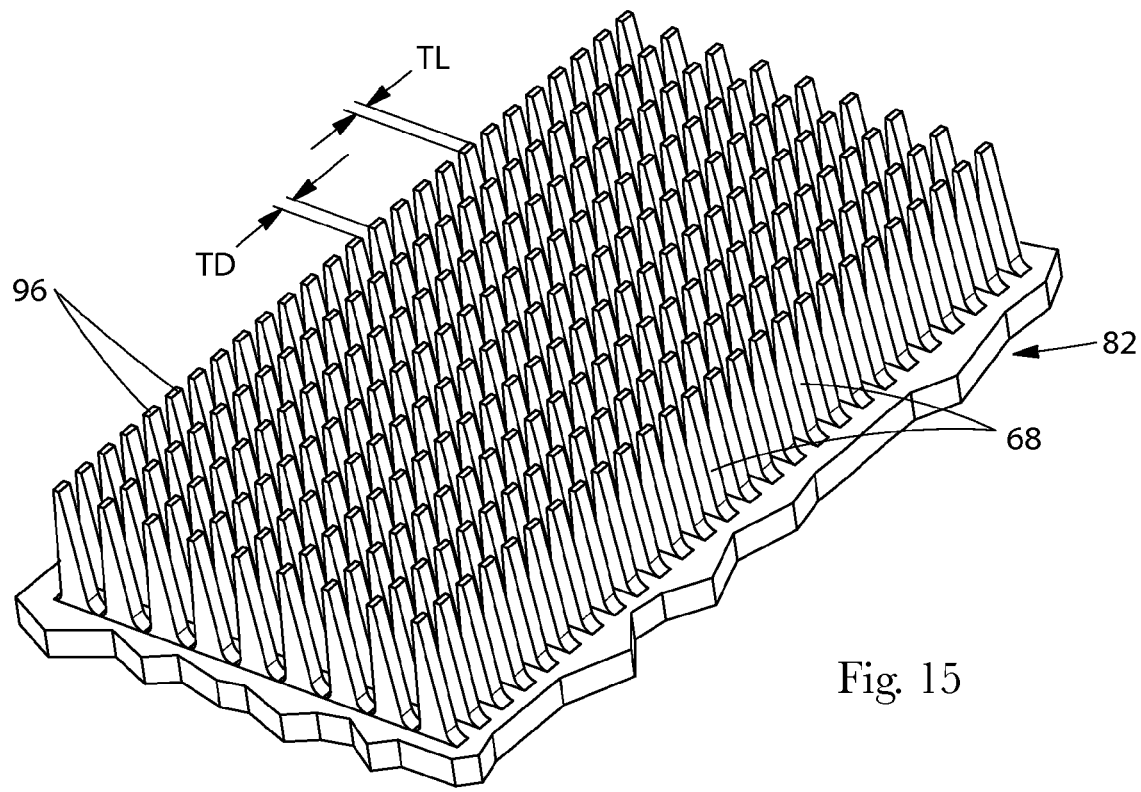
FIG. 15 is a perspective representation of an deformation member for use in a micro-SELF apparatus.
Figure 16:
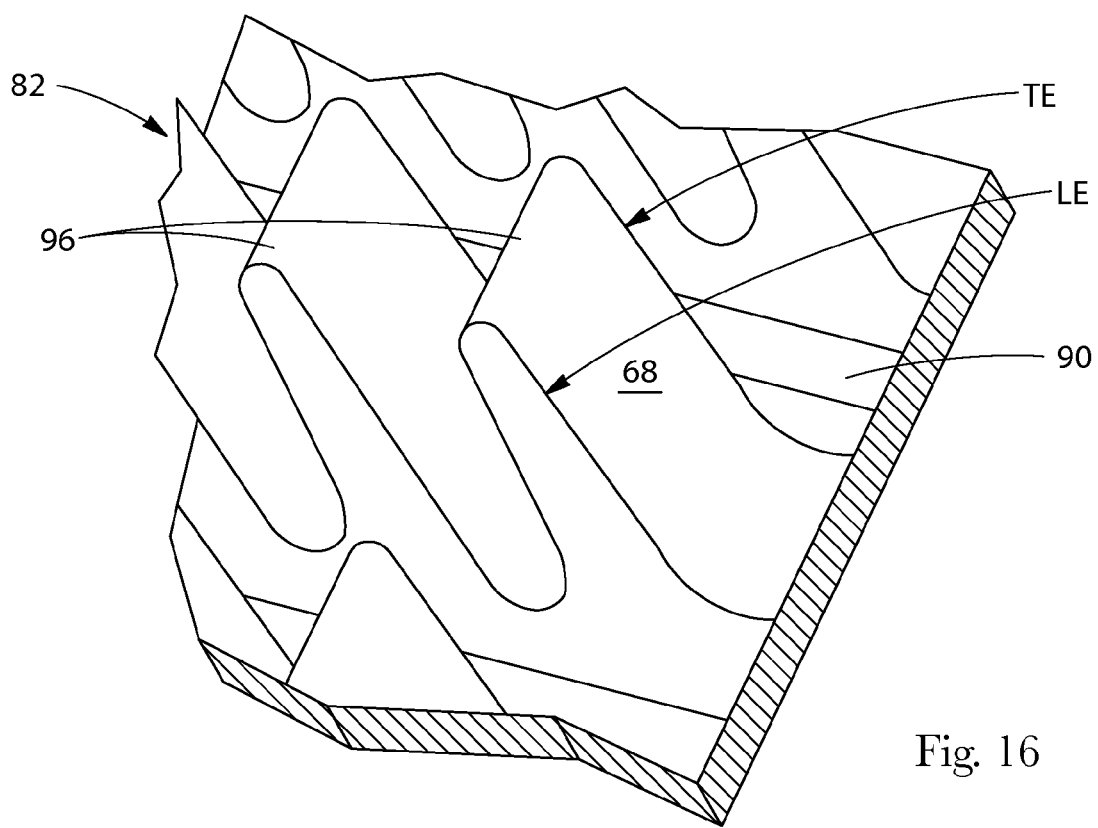
FIG. 16 is an enlarged perspective representation of the teeth on a micro-SELF deformation member.

As shown in the partial perspective view of FIG. 15 and the enlarged partial perspective view of FIG. 16, the teeth 68 of a micro-SELF deformation member 82 have a specific geometry associated with the leading and trailing edges of teeth 68 that permit the teeth to essentially "punch" through the nonwoven web as opposed to, in essence, deforming the web into bumps or teeth as shown in FIGS. 12-14. In some embodiments of a nonwoven web, the teeth 68 urge fibers out-of-plane and to form what can be described as "tufts" or loops of fibers. In one embodiment, the web is punctured, so to speak, by the teeth 68 pushing the fibers through to form tufts or loops. Therefore, unlike the "tent-like" rib-like elements of SELF webs which each have continuous side walls associated therewith, i.e., a continuous "transition zone," the tufts or loops forced out-of-plane in a micro-SELF process can have a discontinuous structure associated with the side wall portions of the Z-direction deformations. Additionally, when utilized for relatively high basis weight absorbent core materials, the "tufting" can be somewhat invisible as fibers are urged out of the plane in a Z-direction with respect to one of the web surfaces, the Z-direction deformation may be muted or non-existent in the other web surface. Further, when a laminate material is involved, the Z-direction deformations of one web material may be pushed into and "hidden" by the second material of the laminate, such that the "tufting" is essentially invisible to the naked eye.

As shown in FIGS. 15 and 16, each tooth 68 has a tooth tip 96, a leading edge LE and a trailing edge TE. The tooth tip 96 is elongated and has a generally longitudinal orientation. It is believed that to get tufted, looped tufts in the processed web, the LE and TE should be very nearly orthogonal to the local peripheral surface 90 of deformation member 82. As well, the transition from the tip 96 and LE or TE should be a sharp angle, such as a right angle, having a sufficiently small radius of curvature such that teeth 68 push through the web at the LE and TE. Without being bound by theory, it is believed that having relatively sharply angled tip transitions between the tip 96 of tooth 68 and the LE and TE permits the teeth 68 to punch through nonwoven webs "cleanly", that is, locally and distinctly, so that one side of the resulting web can be described as "tufted" or otherwise "deformed."

The teeth 68 of a micro-SELF deformation member 82 can have a uniform length dimension TL measured generally from the leading edge LE to the trailing edge TE at the tooth tip 96 of about 1.25 mm and are uniformly spaced from one another circumferentially by a distance TD of about 1.5 mm. For making a terry-cloth web from a web having a total basis weight in the range of about 60 to about 100 gsm, teeth 68 can have a length TL ranging from about 0.5 mm to about 3 mm and a spacing TD from about 0.020 inches (0.5 mm) to about 0.118 inches (3 mm), a tooth height ranging from about 0.020 inches (0.5 mm) to about 0.200 inches (5 mm), and a pitch between about 0.040 inches (1 mm) and about 0.200 inches (5 mm). Depth of engagement can be from about 0.020 inches (0.5 mm) to about 0.200 inches (5 mm) (up to a maximum equal to tooth height). Of course, depth of engagement, pitch, tooth height, TD, and TL can be varied independently of each other to achieve a desired size, spacing, and area density of web deformations as disclosed in co-pending, commonly owned patent applications US 2004/0265534A1, filed Dec. 16, 2003 and US 2005/0123726A1, filed Nov. 3, 2004.

Figure 19:
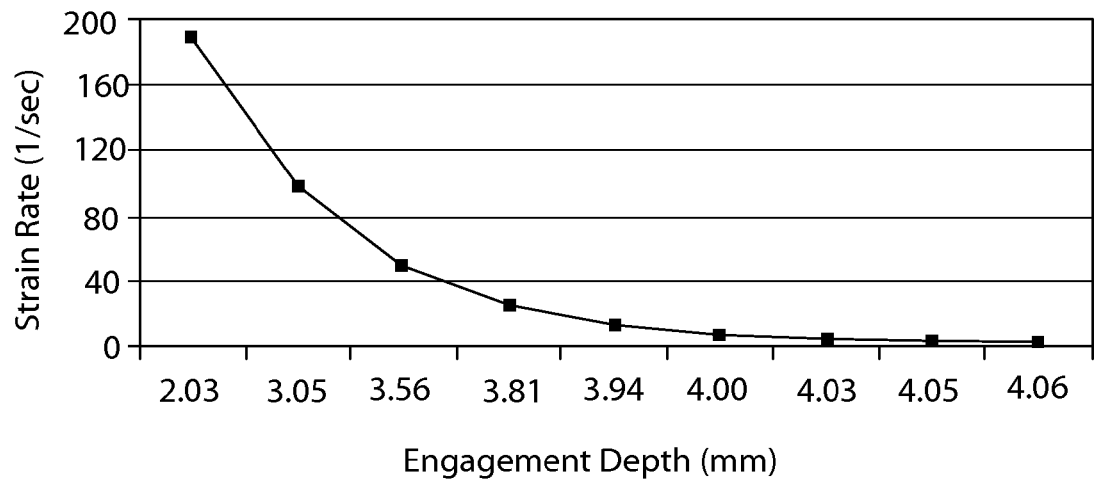
FIG. 19 is a graph showing strain rate varying from high to low in the deformation zone during micro-SELF deformation.
Figures 20A, 20B:
FIG. 20A is a tuft formed in a laminate via micro-SELF deformation according to the strain rate depicted by the graph in FIG. 19.

Using the micro-SELF deformation members according to the present invention, the strain rate in the deformation zone can be controlled to produce web structures exhibiting different tuft and loop formations. For instance, for laminate structure comprising two relatively inextensible materials, the strain rate in the deformation zone can be controlled to vary from low to high as illustrated in the graph in FIG. 17 providing tufts comprising taller loops with blown out tips illustrated in FIG. 18A in comparison to smaller loops with blown out tips formed via high strain rate deformation illustrated in FIG. 18B. Alternatively, for relatively inextensible materials with slightly different extensibilities, varying the strain rate in the deformation zone from a high rate of strain to a low rate of strain as illustrated in the graph in FIG. 19 can result in one of the materials bursting early on resulting in a blown out tip and the other material forming a tall loop extending through the blown out tip illustrated in FIG. 20A in comparison to smaller loops with blown out tips formed via high strain rate deformation illustrated in FIG. 20B.

Figure 21:
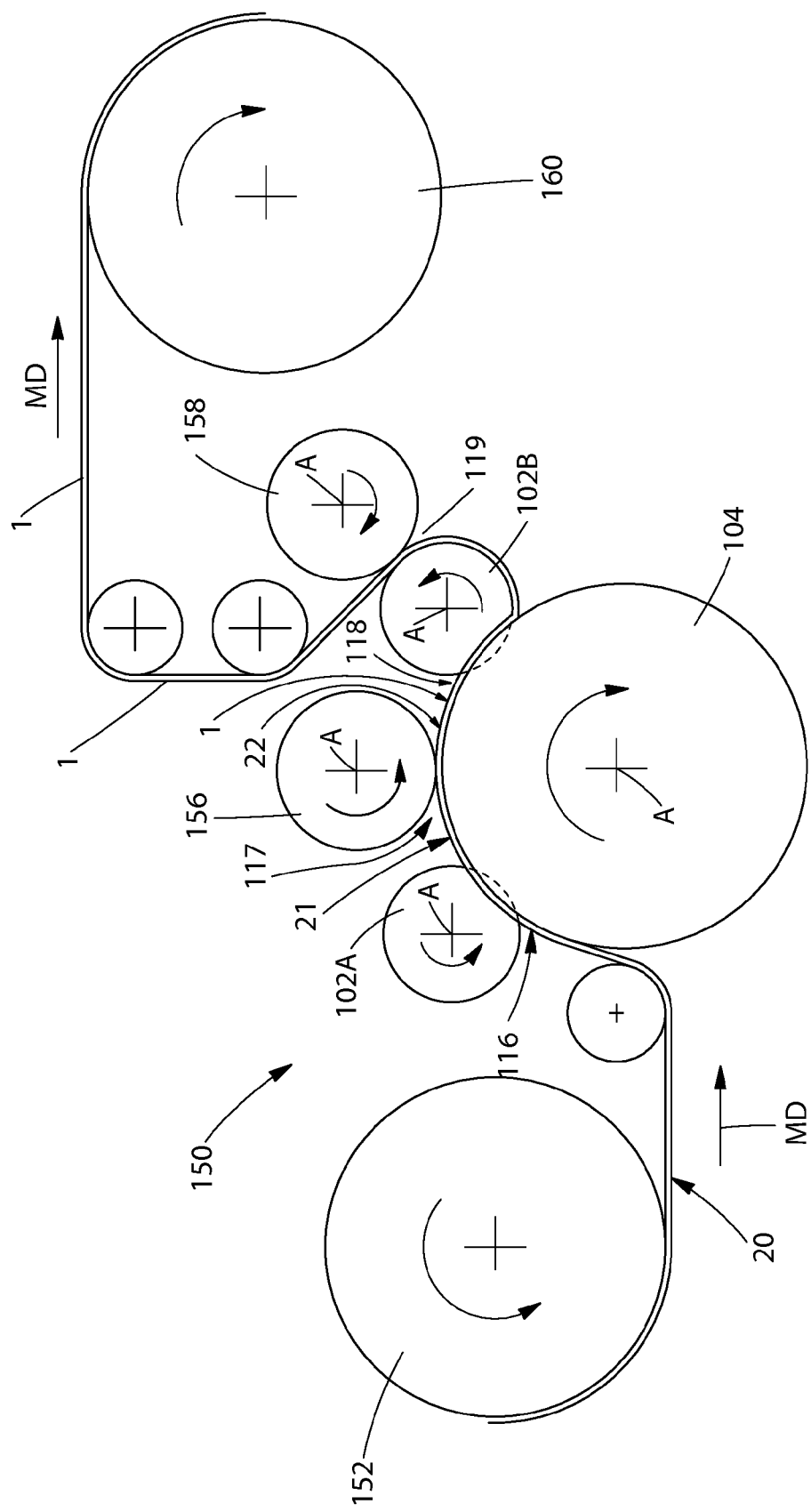
FIG. 21 is a schematic representation of an apparatus to form tufts in a web substrate.

A process using micro-SELF to form tufts in a web substrate is shown in FIG. 21 and disclosed in co-pending, commonly owned patent applications US 2006/0286343A1, filed Jun. 17, 2005. As shown in FIG. 21, structured substrate 1 can be formed from a generally planar, two dimensional nonwoven substrate 20 supplied from a supply roll 152. The web substrate 20 is moved in the machine direction MD by apparatus 150 to a forming apparatus comprising intermeshing rollers 104 and 102A which form tufts at nip 116. The web substrate 21 having tufts proceeds to nip 117 formed between roll 104 and bonding roll 156 which bonds the tips of the tufts. From there, intermediate substrate 22 proceeds to nip 118 formed by intermeshing rolls 102B and 104 which removes intermediate substrate 22 from roll 104 and conveys it to nip 119 formed between roll 102B and bonding roll 158 where bond regions are formed in structured substrate 1 which is eventually taken up on supply roll 160.

Figure 22:
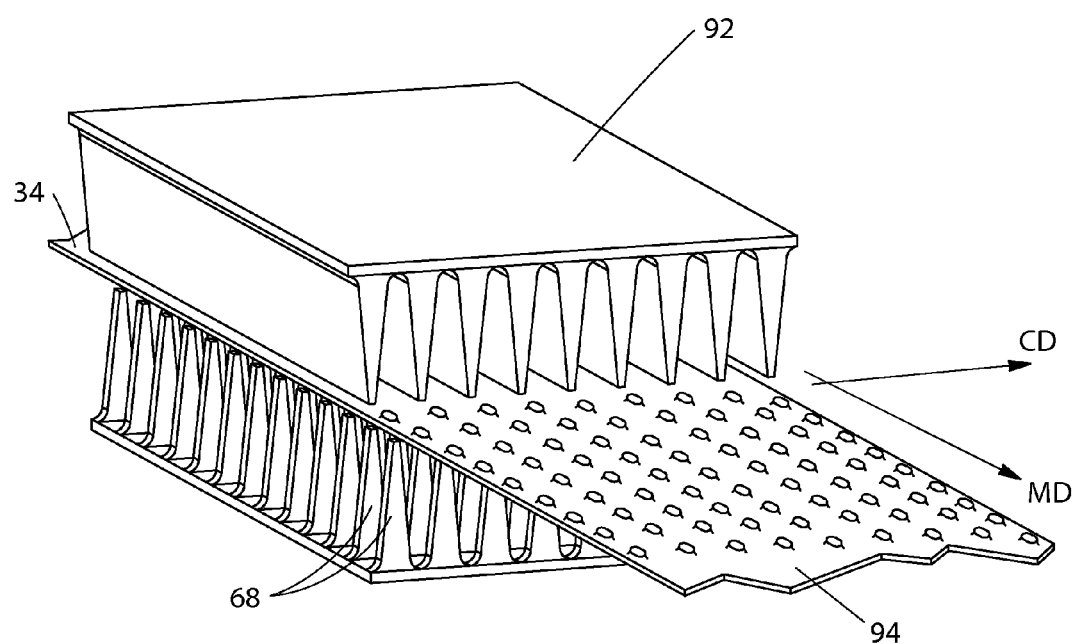
FIG. 22 is a schematic representation of deformation members configured for a rotary knife aperturing.

Another process for mechanically deforming a web which can produce deformed regions and corresponding second activated color regions according to the present invention is a process that can best be described as "rotary knife aperturing" (RKA). In RKA, a process and apparatus using intermeshing deformation members 92 similar to that described above with respect to SELF or micro-SELF deformation members is utilized, as shown in FIG. 22. As shown, the RKA process differs from SELF or micro-SELF in that the relatively flat, elongated teeth of a SELF or micro-SELF deformation member have been modified to be generally pointed at the distal end. Teeth 68, which are preferably heated, can be sharpened to cut through as well as deform web 34 to produce a three-dimensionally apertured web 94 as shown in FIG. 22. In other respects such as tooth height, tooth spacing, pitch, depth of engagement, and other processing parameters, RKA and the RKA apparatus can be the same as described above with respect to SELF or micro-SELF.

Figure 23:
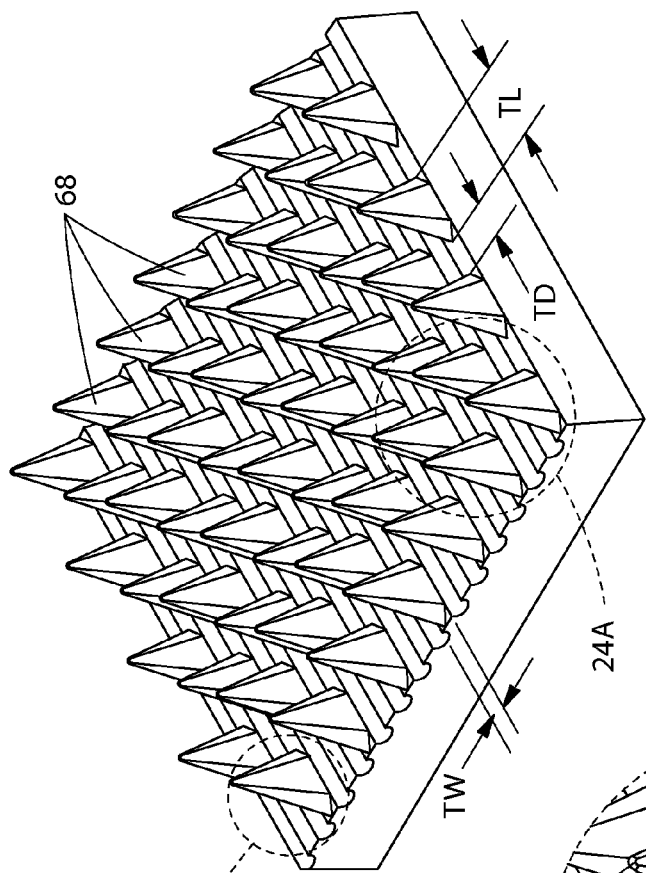
FIG. 23 is a perspective view of a rotary knife aperturing deformation member.
Figure 24A:
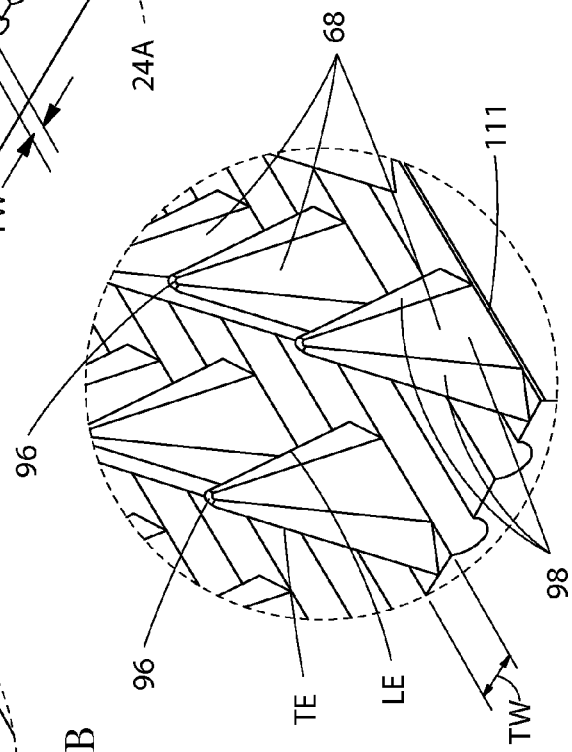
FIG. 24A is an enlarged view of the rotary knife aperturing deformation member shown in FIG. 23.
Figure 24B:
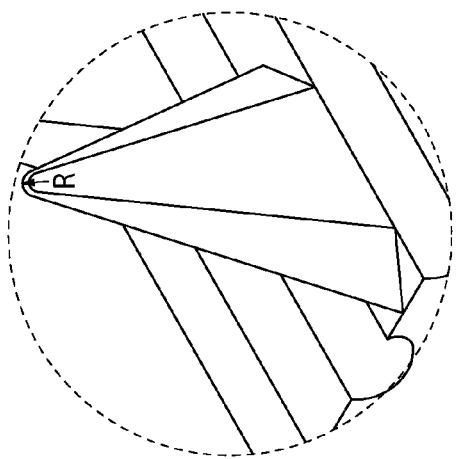
FIG. 24B is an enlarged view of a tooth on the rotary knife aperturing deformation member shown in FIG. 23.

FIG. 23 shows a portion of one embodiment of an RKA toothed deformation member having a plurality of teeth 68 useful for making an apertured web 94. An enlarged view of the teeth 68 is shown in FIGS. 24 A and 24 B. As shown in FIG. 24A, each tooth 68 has a base 111, a tooth tip 96, a leading edge LE and a trailing edge TE. The tooth tip 96 can be generally pointed, blunt pointed, or otherwise shaped so as to stretch and/or puncture the web 34. Teeth 68 can have generally flattened, blade-like shape. Teeth 68 can have generally flattened distinct sides 98. That is, as opposed to round, pin-like shapes that are generally round in cross section, teeth 68 can be elongated in one dimension, having generally non-round, elongated cross-sectional configurations. For example, at their base, teeth 68 can have a tooth length TL and a tooth width TW exhibiting a tooth aspect ratio AR of TL/TW of at least 2, or at least about 3, or at least about 5, or at least about 7, or at least about 10 or greater. In one embodiment, the aspect ratio AR of cross-sectional dimensions remains substantially constant with tooth height.

In one embodiment of an RKA toothed deformation member, teeth 68 can have a uniform length dimension TL of about 0.049 inches (1.25 mm) measured generally from the leading edge LE to the trailing edge TE at the base 111 of the tooth 68, and a tooth width TW of about 0.012 inches (0.3 mm) which is the longest dimension measured generally perpendicularly to the length dimension at the base. Teeth can be uniformly spaced from one another by a distance TD of about 0.059 inches (1.5 mm). For making a soft, fibrous three-dimensional apertured web from a web having a basis weight in the range of from about 5 gsm to about 200 gsm, teeth 68 can have a length TL ranging from about 0.5 mm to about 3 mm, a tooth width TW of from about 0.3 mm to about 1 mm, and a spacing TD from about 0.5 mm to about 3 mm. Similar to the embodiment previously described in reference to FIG. 9, the teeth for the RKA can have a tooth height TH ranging from about 0.5 mm to about 10 mm, and a pitch P between about 1 mm (0.040 inches) and 2.54 mm (0.100 inches). Depth of engagement E can be from about 0.020 inches (0.5 mm) to about 0.200 inches (5 mm) (up to a maximum approaching the tooth height TH).

Of course, E, P, TH, TD and TL can each be varied independently of each other to achieve a desired size, spacing, and area density of apertures (number of apertures per unit area of apertured three-dimensionally apertured web 94). For example, to make apertured films and nonwovens suitable for use in sanitary napkins and other absorbent articles, tooth length TL at the base can range between about 0.08 inches (2.032 mm) to about 0.15 inches (3.81 mm); tooth width TW can range from about 0.02 inches (0.508 mm) to about 0.05 inches (1.27 mm); tooth spacing TD can range from about 0.039 inches (1.0 mm) to about 0.076 inches (1.94 mm); pitch P can range from about 0.044 inches (1.106 mm) to about 0.100 inches (2.54 mm); and tooth height TH can be from about 0.08 inches (2.032 mm) to about 0.27 inches (6.858 mm). Depth of engagement E can be from about 0.020 inches (0.5 mm) to about 0.200 inches (5 mm). The radius of curvature R of the tooth tip 96 shown in FIG. 24B can be from $3.937 \times 10^{-5}$ inches 0.001 mm to about $3.9 \times 10^{-4}$ inches (0.009 mm). Without being bound by theory, it is believed that tooth length TL at the base can range between about 0.01 inches (0.254 mm) to about 0.5 inches (12.7 mm); tooth width TW can range from about 0.01 inches (0.254 mm) to about 0.2 inches (5.08 mm); tooth spacing TD can range from about 0.0 mm to about 1.0 inches (25.4 mm) (or more); pitch P can range from about 0.044 inches (1.106 mm) to about 0.3 inches (7.62 mm); tooth height TH can range from 0.01 inches (0.254 mm) to about 0.709 inches (18 mm); and depth of engagement E can range from 0.01 inches (0.254 mm) to about 0.25 inches (6.35 mm). For each of the ranges disclosed, it is disclosed herein that the dimensions can vary within the range in increments of $3.937 \times 10^{-5}$ (0.001 mm) from the minimum dimension to the maximum dimension, such that the present disclosure is teaching the range limits and every dimension in between in $3.937 \times 10^{-5}$ inch (0.001 mm) increments (except for radius of curvature R, in which increments are disclosed as varying in $3.937 \times 10^{-5}$ inch (0.0001 mm) increments).

RKA teeth can have other shapes and profiles and the RKA process can be used to aperture fibrous webs, as disclosed in co-pending, commonly owned patent applications US 2005/0064136A1, filed Aug. 6, 2004, US 2006/0087053A1, filed Oct. 13, 2005, and US 2005/021753 filed Jun. 21, 2005.

Another process for mechanically deforming a web which can produce deformed regions comprising apertures according to the present invention is a process which uses a pin roll and a counter roll that rotate in opposite directions to form a nip through which the web substrate is fed as disclosed in U.S. Pat. No. 6,849,319. Pins protrude from the surface of the pin roll and holes are recessed into the counter roll. The pin roll and the counter roll are aligned so that pins of the pin roll mate with the holes of the counter roll. The pins may be heated. The method utilizing the pin roll and counter roll can be used to form apertured webs.

Another process for mechanically deforming a web substrate according to the present invention is embossing. Embossing of webs can provide improvements to the web such as increased bulk. During a typical embossing process, a web is fed through a nip formed between juxtaposed generally axially parallel rolls. Embossing elements on the rolls compress and/or deform the web. The embossed regions of the plies may produce an aesthetic pattern and provide a means for joining and maintaining the plies in face-to-face contacting relationship.

Embossing is typically performed by one of two processes; knob-to-knob embossing or nested embossing. Knob-to-knob embossing typically consists of generally axially parallel rolls juxtaposed to form a nip between the embossing elements on opposing rolls. Nested embossing typically consists of embossing elements of one roll meshed between the embossing elements of the other roll. Examples of knob-to-knob embossing and nested embossing are illustrated in the prior art by U.S. Pat. No. 3,414,459 issued Dec. 3, 1968 to Wells; U.S. Pat. No. 3,547,723 issued Dec. 15, 1970 to Gresham; U.S. Pat. No. 3,556,907 issued Jan. 19, 1971 to Nystrand; U.S. Pat. No. 3,708,366 issued Jan. 2, 1973 to Donnelly; U.S. Pat. No. 3,738,905 issued Jun. 12, 1973 to Thomas; U.S. Pat. No. 3,867,225 issued Feb. 18, 1975 to Nystrand; U.S. Pat. No. 4,483,728 issued Nov. 20, 1984 to Bauernfeind; U.S. Pat. No. 5,468,323 issued Nov. 21, 1995 to McNeil; U.S. Pat. No. 6,086,715 issued Jun. 11, 2000 to McNeil; U.S. Pat. No. 6,277,466 Aug. 21, 2001; U.S. Pat. No. 6,395,133 issued May 28, 2002 and U.S. Pat. No. 6,846,172 B2 issued to Vaughn et al. on Jan. 25, 2005.

The web substrates having activatable colorants according to the present invention are applicable, but not limited to absorbent articles such as diapers, sanitary napkins, tampons, panty liners, incontinence devices, wipes and the like. For absorbent articles, the web substrates having activatable colorants can include topsheets, secondary topsheets, acquisition layers absorbent cores and backsheets. Alternatively, the web substrates can be applicable to various components of the absorbent article such as fasteners, barrier cuffs, and landing zones. In addition to absorbent articles, web substrates having activatable colorants according to the present invention are applicable to trash bags, packaging films and dryer sheets.

The color of the first activated colored region and second activated colored region in a web substrate can be measured by the reflectance spectrophotometer according to the colors $L^*$, $a^*$, and $b^*$ values. The $L^*$, $a^*$, and $b^*$ values are measured from the surface of a web substrate. The difference in color is calculated using the $L^*$, $a^*$, and $b^*$ values by the formula $\Delta E=[(L^*X.-L^*Y)2+(a^*X.-a^*Y)2+(b^*X-b^*Y)2]\frac{1}{2}$. Herein, the 'X' in the equation may represent the first activated colored region or the second activated colored region and 'Y' may represent the color of another region against which the color of such region is compared. X and Y should not be the same two points of measurement at the same time. In other words, for any particular comparison of the difference in color, the location of X does not equal (≠) the location of Y.

Where more than two colors are used, the 'X' and 'Y' values alternately include points of measurement in them also. The key to the $\Delta E$ calculation herein is that the 'X' and 'Y' values should not stem from the same measured point on the viewing surface. In those instances where there is effectively no non-colored portion within the confines of the measurement area, the 'X' values should flow from a point different in spatial relationship to the 'Y' values.

Reflectance color can be measured using the Hunter Lab LabScan XE reflectance spectrophotometer obtained from Hunter Associates Laboratory of Reston, Va. A web substrate is tested at an ambient temperature between 65° F. and 75° F. and a relative humidity between 50% and 80%.

The spectrophotometer is set to the CIELab color scale and with a D65 illumination. The Observer is set at 10° and the Mode is set at 45/0°. Area View is set to 0.125" and Port Size is set to 0.20" for films; Area View is set to 1.00" and Port Size is set to 1.20" for nonwovens and other materials. The spectrophotometer is calibrated prior to sample analysis utilizing the black and white reference tiles supplied from the vendor with the instrument. Calibration is done according to the manufacturer's instructions as set forth in LabScan XE User's Manual, Manual Version 1.1, August 2001, A60-1010-862. If cleaning is required of the reference tiles or samples, only tissues that do not contain embossing, lotion, or brighteners should be used (e.g., PUFFS tissue). Any sample point on the absorbent article containing the activated color to be analyzed can be selected.

The web substrate is placed over the sample port of the spectrophotometer with a white tile placed behind the web substrate. The web substrate is to be in a substantially flat condition and free of wrinkles.

The web substrate is removed and repositioned so that a minimum of six readings of color of the web substrate are conducted. If possible (e.g., the size of the activated color on the element in question does not limit the ability to have six discretely different, non-overlapping sample points), each of the readings is to be performed at a substantially different region on the externally visible surface so that no two sample points overlap. If the size of the activated colored region requires overlapping of sample points, only six samples should be taken with the sample points selected to minimize overlap between any two sample points. The readings are averaged to yield the reported $L^*$, $a^*$, and $b^*$ values for a specified color on an externally visible surface of an element.

In calculating the CIELab color space volume, V, maximum and minimum $L^*$, $a^*$, and $b^*$ values reported are determined for a particular set of regions to be measured. The maximum and minimum $L^*$, $a^*$, and $b^*$ values reported are used to calculate the CIELab color space volume, V according to the following formula:

$$V = \frac{4}{3}\left|\frac{\Delta L^*}{2}\right|\left\|\frac{\Delta a^8}{2}\right\|\left|\frac{\Delta b^*}{2}\right|$$

Within the above formula, $\Delta L^*$ is the difference in $L^*$ values between the two colored regions being compared and is calculated by: $\Delta L^*=L^*X-L^*Y$. The $\Delta a^*$ is the difference in $a^*$ values between the two colored regions being compared and is calculated by: $\Delta a^*=a^*X-a^*Y$. The $\Delta b^*$ is the difference in $b^*$ values between the two colored regions being compared and is calculated by: $\Delta b^*=b^*X-b^*Y$. The CIELab color space volume can result in a solid substantially ellipsoidal in shape. If $\Delta L^*$, $\Delta a^*$, and $\Delta b^*$ are equal, the solid will be spherical. As used herein, a "solid" refers to the mathematical concept of a three-dimensional figure having length, breadth, and height (or depth). An ellipsoidal volume is preferred to calculate volume because an ellipsoid generally requires the dimensional differences of $\Delta L^*$, $\Delta a^*$, and $\Delta b^*$ to be relatively more uniform than other solids. Furthermore, it is believed that ellipsoidal volumes are more visually acceptable (i.e., less detectable color mismatch by human perception) than spherical volumes.

In some embodiments, the activated colors of at least two externally visible surfaces of discrete elements will occupy a CIELab color space volume of less than about 200. The externally visible surfaces are analyzed according to the Test Method described above. Upon analysis, the inherent color of an element comprising an externally visible surface will yield $L^*$, $a^*$, and $b^*$ coordinates. The CIELab color space volume is then calculated using the formula presented above. The resulting volume can be less than about 200. The resulting volume can be less than about 50.

It should be recognized that the activated colors of more than two discrete colored regions may occupy the aforementioned CIELab color space volumes. In calculating the CIELab color space volume for more than two elements, the CIELab color space volume is calculated using the maximum and minimum $L^*$, $a^*$, and $b^*$ from a set of elements. The maximum color values and minimum color values are used to calculate V according to the formula presented above.

Method of Color Measurement:

Each sample was laid flat and face down upon a Hewlett-Packard ScanJet 6300C scanner. The scanner lid was closed completely upon each sample and the sample was scanned.

The resulting scanned sample images were saved under the "True Color" setting. Standards were measured the same way using the white and green Hunter tile numbers LX16566. The sample images were analyzed using Image J imaging and analysis software, ten locations within each distinct color region were sampled at random for each sample. Colors were measured in RGB color space. The RGB values were then mathematically transformed to XYZ and then to cieL*a*b* color space using the following algorithms:

Convert RGB to XYZ (Observer=2°, Illuminant=D65)

Reference: "A Standard Default Color Space for the Internet—sRGB" Michael Stokes (Hewlett-Packard), Matthew Anderson (Microsoft), Srinivasan Chandrasekar (Microsoft), Ricardo Motta (Hewlett-Packard) Version 1.10, Nov. 5, 1996 http://www.w3.org/Graphics/Color/sRGB 1. Convert from 8-bit RGB: Image J measures RGB in 8-bit. This step converts 8-bit to 0-1 scale for sRGB.

var_R=(R/255) //R from 0 to 255
var_G=(G/255) //G from 0 to 255
var_B=(B/255) //B from 0 to 255

2. Linearize RGB values to arrive at standard RGB (sRGB): RGB is a non-linear measurement. In order to linearize the expression in XYZ color-coordinate space this equation is employed.

if (var_R>0.04045) var_R=((var_R+0.055)/1.055)^2.4
else var_R=var_R/12.92
if (var_G>0.04045) var_G=((var_G+0.055)/1.055)^2.4
else var_G=var_G/12.92
if (var_B>0.04045) var_B=((var_B+0.055)/1.055)^2.4
else var_B=var_B/12.92

3. Convert to 0-100 XYZ scale: XYZ is in a 0-100 scale. This converts to that scale.

var_R=var_R*100
var_G=var_G*100
var_B=var_B*100

4. Derived relationship for sRGB to XYZ tristimulus values: This is the multiplication array that describes the relationship between sRGB and XYZ when an object is illuminated with D65.

//Observer.=2°, Illuminant=D65
X=var_R*0.4124+var_G*0.3576+var_B*0.1805
Y=var_R*0.2126+var_G*0.7152+var_B*0.0722
Z=var_R*0.0193+var_G*0.1192+var_B*0.9505
XYZ to cieL*a*b* (Observer=2°, Illuminant=D65)

Reference: ISO Standard 13655 International Organization for Standardization, ISO Geneva. "ISO 13655:1996 Graphic Technology-Spectral Measurement and Colorimetric Computation for Graphic Arts Images" (1996).

1. Defines Slope in XYZ Color Coordinate Space
var_X=X/ref_X //ref_X=95.047
var_Y=Y/ref_Y //ref_Y=100.000
var_Z=Z/ref_Z //ref_Z=108.883

2. Current Iso Standard for Converting Between XYZ and L*a*b* if (var_X>0.008856) var_X=var_X^(⅓)
else var_X=(7.787*var_X)+(16/116)
if (var_Y>0.008856) var_Y=var_Y^(⅓)
else var_Y=(7.787*var_Y)+(16/116)
if (var_Z>0.008856) var_Z=var_Z^(⅓)
else var_Z=(7.787*var_Z)^(16/116)
CIE-L*=(116*var_Y)−16
CIE-a*=500*(var_X−var_Y)
CIE-b*=200*(var_Y−var_Z)

For each sample image, the delta L*, delta a*, and delta b* were calculated between the two distinct color regions using the following formula:
Delta L*=L*color 1−L*color 2
Delta a*=a*color 1−a*color 2
Delta b*=b*color 1−b*color 2

Total color differences (delta E*) between the two distinct color regions for each sample were then calculated using the following formula:

$$\text{Delta } E^* = [(\text{Delta } L^*)^2 + (\text{Delta } a^*)^2 + (\text{Delta } b^*)^2]^{1/2}$$

EXAMPLES

The following non-limiting examples are intended to illustrate potential embodiments of the present invention.

Example 1

SELFed Nonwoven

A spunbond nonwoven fabric was prepared comprising polypropylene and 2 weight percent Datalase Colour Change Pigment LT. Basis weight of the nonwoven is 62 grams per square meter. As made, the nonwoven is white. A handsheet of this nonwoven material was UV activated to produce a uniform blue color throughout the sample. This was done in a Chromato-Vue C-75 UV darkroom cabinet set to 254 nm with an exposure time of 30 seconds. The nonwoven was subsequently SELFed using a 0.060 inch pitch 13 tooth diamond pattern with a depth of engagement of 0.110 inches at hand-crank speed. The resulting material has a plurality of ridges and grooves which are pink, surrounded by undeformed regions that are blue. Color measurements and ΔE values are provided in Table 1. FIGS. 1 and 2 are black and white photographs of the material.

Example 2

Tufted Nonwoven

The same nonwoven as in Example 1 was similarly activated by UV to a uniform purple color via 2 minutes exposure in a Chromato-Vue C-75 UV darkroom cabinet set to 254 nm. Instead of SELFing, the nonwoven was hand cranked through a 0.060 inch pitch micro-SELF unit (similar to that in FIG. 21) to form a tufted structure. The resulting material has a plurality of tufts that are pink, surrounded by undeformed regions that are purple. Color measurements and ΔE values are provided in Table 1. FIG. 3 is a black and white photograph of the material.

Example 3

Apertured Nonwoven

The same nonwoven as in Example 1 was similarly activated by UV to a uniform blue color. Instead of SELFing, the nonwoven was hand cranked through 0.100 inch pitch heated rotary knife aperturing tooling at a depth of engagement of 0.150 inches. Both the top and bottom rolls were heated to 270° F. The resulting nonwoven has apertures that are pink around their perimeters while the surrounding nonwoven is blue. Color measurements and ΔE values are provided in Table 1. FIG. 4 is a black and white photograph of the material.

Example 4

Apertured Nonwoven

A spunbond nonwoven fabric was prepared comprising polypropylene and 0.5 weight percent Datalase Colour Change Pigment HT. Basis weight of the nonwoven is 48 grams per square meter. As made, the nonwoven is white. A hand sheet of this nonwoven material was UV activated to produce a uniform blue color throughout the sample. This was done in a Chromato-Vue C-75 UV darkroom cabinet set to 254 nm with an exposure time of 1 minute. A hand sheet of this nonwoven was hand cranked through 0.100 inch pitch heated rotary knife aperturing tooling at a depth of engagement of 0.150 inches. Both the top and bottom rolls were heated to 270° F. The resulting nonwoven has apertures that are pink around their perimeters while the surrounding nonwoven is blue. Color measurements and ΔE values are provided in Table 1.

Example 5

Nonwoven with Ultrasonic Bonding

The same nonwoven as in Example 1 was similarly activated by UV to a uniform blue color. The nonwoven was then pattern bonded using a Branson ultrasonic scanner. The bond sites turned pink while the remainder of the nonwoven stayed blue. Color measurements and ΔE values are provided in Table 1. FIG. 5 is a black and white photograph of the material.

Example 6

Nonwoven with Ultrasonic Bonding

The same nonwoven as in Example 4 was similarly activated by UV to a uniform blue color. The nonwoven was then pattern bonded using a Branson ultrasonic scanner. The bond sites turned pink while the remainder of the nonwoven stayed blue. Color measurements and ΔE values are provided in Table 1.

TABLE 1

| Example | First (Undeformed) Region | | | Second (Deformed) Region | | | |
|---|---|---|---|---|---|---|---|
| | L* | a* | b* | L* | a* | b* | ΔE |
| 1 | 75.76 | 4.71 | −31.31 | 74.77 | 10.84 | −22.44 | 11.15 |
| 2 | 68.15 | 12.85 | −32.68 | 79.10 | 14.76 | −19.08 | 17.56 |
| 3 | 73.60 | 10.82 | −29.77 | 73.38 | 26.38 | −17.38 | 19.89 |
| 4 | 79.83 | 3.42 | −20.79 | 73.86 | 18.20 | −16.69 | 16.47 |
| 5 | 70.79 | 11.59 | −32.37 | 79.64 | 28.03 | −12.44 | 27.32 |
| 6 | 75.76 | 4.71 | −31.31 | 73.41 | 18.74 | −24.00 | 15.99 |

Example 7

SELF'ed Nonwoven with Color Zones

The same nonwoven as in Example 1 was activated by UV via 2 minutes exposure in a Chromato-Vue C-75 UV darkroom cabinet set to 254 nm. Instead of uniform exposure, a stencil was used to selectively mask some areas from the UV light. The resultant nonwoven had a pattern of white ducks, clouds and suns on a purple background. The nonwoven was subsequently SELF'ed using a 0.060 inch pitch small circle SELF pattern with a depth of engagement of 0.135 inches at hand crank speed. Within the purple regions (which had been exposed to UV), the resulting ridges and grooves turned pink whereas in the white regions that were not exposed to UV, the resulting ridges and grooves remained white. Color measurements and ΔE values for the zone exhibiting the color change are provided in Table 2. FIG. 6 is a black and white photograph of the material.

TABLE 2

| Example 7 | First (Undeformed) Region | | | Second (Deformed) Region | | | |
|---|---|---|---|---|---|---|---|
| | L* | a* | b* | L* | a* | b* | ΔE |
| Purple Zone | 54.85 | 10.08 | −26.57 | 58.37 | 10.29 | −15.65 | 11.48 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or patent application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A web substrate having activated color regions and at least one deformed region, wherein said web substrate comprises:
   (a) a first activated color region produced in response to a first external stimulus;
   (b) at least one deformed region located within the first activated color region; and
   (c) a second activated color region located within said at least one deformed region.

2. The web substrate of claim 1 wherein the activated color regions are produced from activatable colorant having both photoreactive and thermochromic material properties.

3. The web substrate according to claim 1 wherein the first external stimulus comprises electromagnetic radiation.

4. The web substrate of claim 1 wherein the second activated color region is formed in response to a second external stimulus comprising heat induced by strain during formation of the at least one deformed region.

5. The web substrate of claim 1 wherein the web substrate is selected from the group consisting of films, nonwovens, laminates, fibers, and foams.

6. The web substrate according to claim 1 further comprising a plurality of deformed regions within the first activated color region wherein the plurality of deformed regions include a plurality of second activated color regions coinciding with the plurality of deformed regions.

7. The web substrate of claim 6 wherein the activated color regions include multiple color patterns, zone patterns and multiple shades of a single color.

8. The web substrate according to claim 6 wherein the plurality of deformed regions comprises apertures extending through the web substrate and the second activated color regions surround the perimeters of the apertures.

9. The web substrate according to claim 6 wherein the web substrate is planar in the x-y plane and the plurality of deformed regions protrude in a z direction out of the x-y plane.

10. The web substrate according to claim 9 wherein the plurality of deformed regions comprises ridges and grooves.

11. The web substrate according to claim 9 wherein the plurality of deformed regions comprise tufts.

12. An absorbent article comprising:
(a) the web substrate of claim 1; and
(b) a package containing said article.

13. A web substrate having activated color regions and deformed regions, wherein said web substrate comprises:
(a) a first activated color region formed in response to a first external stimulus comprising electromagnetic radiation;
(b) a plurality of deformed regions located within the first activated color region, wherein said plurality of deformed regions are separated by undeformed regions; and
(c) a plurality of second activated color regions that coincide with the deformed regions.

14. The web substrate of claim 13 wherein the plurality of second activated color regions are formed in response to a second external stimulus wherein the second external stimulus comprises heat induced by strain during formation of the deformed regions.

15. The web substrate of claim 13 wherein the web substrate comprises a thermoplastic material.

16. The web substrate according to claim 13 wherein the plurality of deformed regions comprise alternating rib-like elements.

17. The web substrate according to claim 13 wherein the web substrate comprises a fibrous web and wherein the deformed regions comprise a plurality of tufted fibers integral with and extending from the first activated color region.

18. The web substrate according to claim 13 wherein the plurality of deformed region comprises apertures extending through the web substrate and the activated color regions surround the perimeters of the apertures.

19. The web substrate according to claim 13 wherein the web substrate comprises a film and wherein the deformed regions comprise three dimensional, volcano shaped apertures.

20. An absorbent article comprising:
(a) the web substrate of claim 13; and
(b) a package containing said article.

21. A web substrate having activated color regions and at least one deformed region, wherein said web substrate comprises:
(a) a first activated color region having a first color produced in response to a first external stimulus comprising electromagnetic radiation;
(b) at least one deformed region located within the first activated color region; and
(c) a second activated color region having a second color produced in response to a second external stimulus induced by formation of the at least one deformed region, wherein said second activated color region coincides with the deformed region.

22. The web substrate according to claim 21 wherein the electromagnetic radiation comprises ultraviolet light and the second external stimulus comprises heat induced by strain.

23. An absorbent article comprising:
(a) the web substrate of claim 21; and
(b) a package containing said article.

* * * * *